(12) United States Patent  (10) Patent No.: US 8,048,142 B2
Venturelli  (45) Date of Patent: Nov. 1, 2011

(54) ENDOLUMENAL PROSTHESIS

(75) Inventor: Andrea Venturelli, Concesio (IT)

(73) Assignee: Invatec S.r.l., Roncadelle (Brescia) (IT)

( * ) Notice: Subject to any disclaimer, the term of this patent is extended or adjusted under 35 U.S.C. 154(b) by 208 days.

(21) Appl. No.: 11/931,302

(22) Filed: Oct. 31, 2007

(65) Prior Publication Data

US 2008/0132997 A1 Jun. 5, 2008

Related U.S. Application Data

(63) Continuation of application No. 10/538,913, filed as application No. PCT/IT02/00813 on Dec. 19, 2002.

(51) Int. Cl.
*A61F 2/06* (2006.01)
(52) U.S. Cl. ..................... 623/1.15; 623/1.42
(58) Field of Classification Search ................. 623/1.11, 623/1.12, 1.15, 1.18, 1.2, 1.37, 1.16, 1.42
See application file for complete search history.

(56) References Cited

U.S. PATENT DOCUMENTS

| 4,733,665 | A | 3/1988 | Palmatz |
| 4,739,762 | A | 4/1988 | Palmatz |
| 4,800,882 | A | 1/1989 | Gianturco |
| 4,907,336 | A | 3/1990 | Gianturco |
| 5,035,706 | A | 7/1991 | Gianturco et al. |
| 5,037,392 | A | 8/1991 | Hillstead |
| 5,041,126 | A | 8/1991 | Gianturco |
| 5,102,417 | A | 4/1992 | Palmatz |
| 5,147,385 | A | 9/1992 | Beck et al. |
| 5,282,824 | A | 2/1994 | Gianturco |
| 5,316,023 | A | 5/1994 | Palmatz et al. |
| 5,935,162 | A | 8/1999 | Dang |
| 6,299,604 | B1 | 10/2001 | Ragheb et al. |
| 6,540,775 | B1 | 4/2003 | Fischell et al. |
| 7,220,275 | B2 * | 5/2007 | Davidson et al. ............ 623/1.35 |
| 2002/0007212 | A1 * | 1/2002 | Brown et al. ................ 623/1.16 |
| 2002/0035392 | A1 * | 3/2002 | Wilson ......................... 623/1.11 |
| 2002/0065547 | A1 | 5/2002 | Moore |
| 2002/0183763 | A1 | 12/2002 | Callol et al. |
| 2003/0018377 | A1 * | 1/2003 | Berg et al. ................... 623/1.11 |
| 2004/0167608 | A1 * | 8/2004 | Cheng ......................... 623/1.15 |

FOREIGN PATENT DOCUMENTS

| CA | 1239755 | 8/1988 |
| CA | 1245527 | 11/1988 |
| CA | 2134997 | 5/1996 |
| CA | 2171047 | 9/1997 |
| CA | 2192520 | 9/1997 |
| CA | 2175722 | 11/1997 |
| CA | 2185740 | 3/1998 |
| EP | 0888093 | 1/1999 |
| EP | 0895760 | 2/1999 |

(Continued)

OTHER PUBLICATIONS

Edited by: Sigwart, U., et al.; Handbook of Cardiovascular Interventions; 1996; pp. 547-679; Churchill Livingstone; Edinburgh, United Kingdom.

(Continued)

*Primary Examiner* — S. Thomas Hughes
*Assistant Examiner* — Thomas McEvoy

(57) ABSTRACT

An expandable endolumenal prosthesis comprises, in its non-expanded configuration, a tubular body extending along a longitudinal axis and having a distal end and a proximal end. The tubular body having a porous wall defined by a plurality of interlaced circumferential lines forming a pathway motif or pattern.

23 Claims, 25 Drawing Sheets

FOREIGN PATENT DOCUMENTS

| | | |
|---|---|---|
| EP | 1095633 | 5/2001 |
| EP | 1151730 | 11/2001 |
| EP | 0956832 | 11/2007 |
| WO | 97/25937 | 7/1997 |
| WO | 97/32543 | 9/1997 |
| WO | 97/32544 | 9/1997 |
| WO | 97/41803 | 11/1997 |
| WO | 98/47447 | 10/1998 |

OTHER PUBLICATIONS

Colombo, A., et al.; Techniques in Coronary Artery Stenting; 2000; pp. 39-71; Martin Dunitz Ltd; United Kingdom.

* cited by examiner

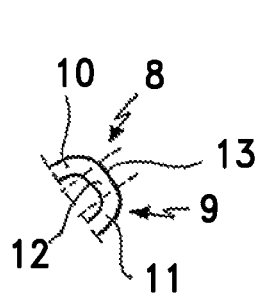
FIG.4bis
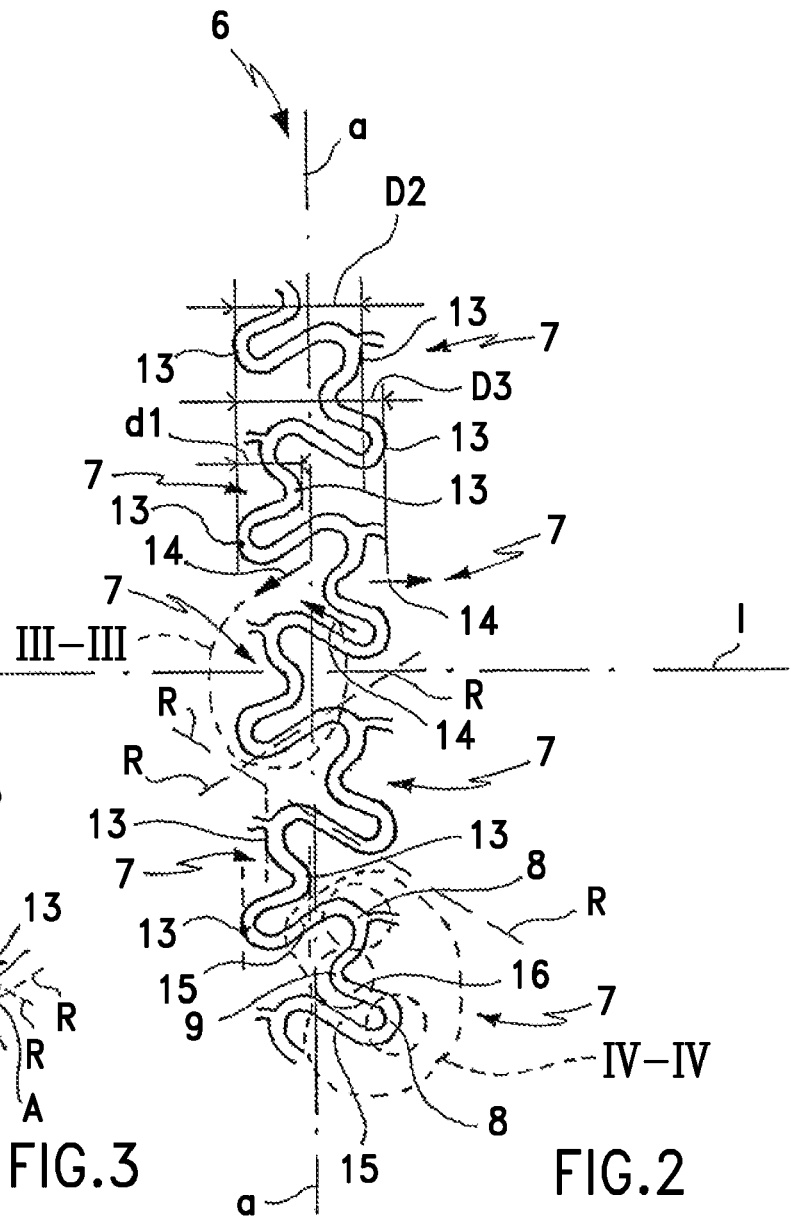
FIG.2
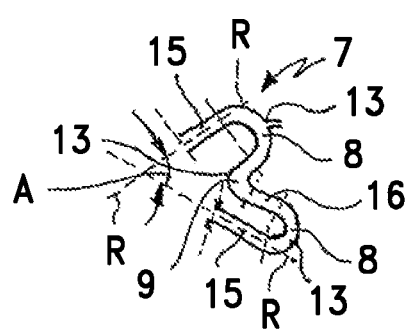
FIG.3
FIG.4

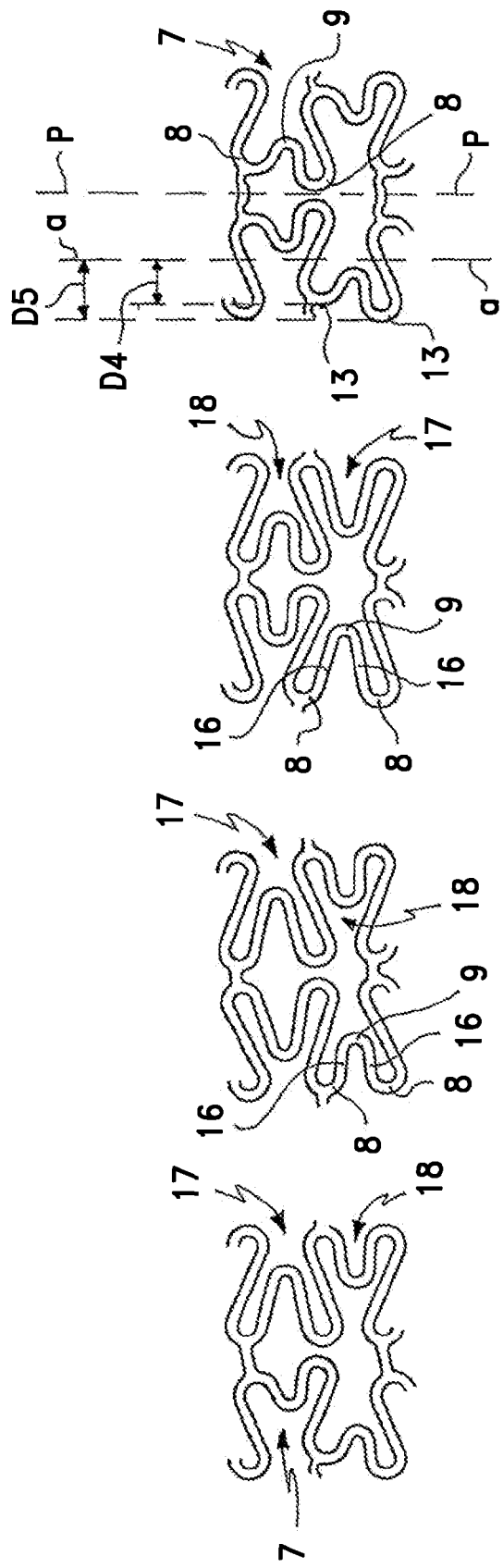

ENDOLUMENAL PROSTHESIS

This application is a continuation of copending application Ser. No. 10/538,913, which is the U.S. national stage of international application PCT/IT2002/000813, filed Dec. 19, 2002.

FIELD OF THE INVENTION

The subject of the present invention is an expandable endolumenal prosthesis.

BACKGROUND OF THE INVENTION

This term defines, in general, a device which is inserted in a lumen, for example, a vascular duct and, in particular, an arterial duct, usually by means of an endolumenal-prosthesis transport system, or stent delivery system (SDS), and is then expanded or spread out in situ in order to support the walls of the lumen locally. The main object of this support is to eliminate the blockage, for example, brought about by a stenosis, and to prevent the re-formation thereof.

A general treatise on endolumenal prostheses or stents can be found in the works "Techniques in coronary artery stenting" by Colombo and Tobis, Martin Dumitz Ltd., 2000 and "Handbook of cardiovascular interventions" by Ulrich Sigwart, Michel Bertrand, Patrick W. Serruys, Harcourt Brace & Company Limited, 1996.

Endovascular prostheses are generally known. However, the term "endovascular prosthesis" has been used interchangeably with other terms such as "stent" or "expandable prosthesis". The term "vascular prosthesis" used in this description should be understood as including any expandable prosthetic device for implantation in a human or animal duct (such as, for example, a lumen, an artery, a vessel, a respiratory duct, a gastrointestinal duct, a bile duct, or the like).

A large number of patent documents relating to endolumenal prostheses have been filed in the past, for example: U.S. Pat. No. 4,733,665 (Palmatz), U.S. Pat. No. 4,739,762 (Palmatz), U.S. Pat. No. 4,800,882 (Gianturco), U.S. Pat. No. 4,907,336 (Gianturco), U.S. Pat. No. 5,035,706 (Gianturco et al.), U.S. Pat. No. 5,037,392 (Hillstead), U.S. Pat. No. 5,041,126 (Gianturco), U.S. Pat. No. 5,102,417 (Palmatz), U.S. Pat. No. 5,147,385 (Beck et al.), U.S. Pat. No. 5,282,824 (Gianturco), U.S. Pat. No. 5,316,023 (Palmatz et al.), CA 1,239,755 (Wallsten), CA 1,245,527 (Gianturco et al.), CA 2,134,997 (Penn et al.), CA 2,171,047 (Penn et al.), CA 2,175,722 (Penn et al.), CA 2,185,740 (Penn et al.), CA 2,192,520 (Penn et al.), PCT/CA97/00151 (Penn et al.), PCT/CA97/00152 (Penn et al.), PCT/CA97/00294 (Penn et al.), EP 0 895 760 (Bartorelli), EP 0 888 093 (Penn et al.), EP 1 151 730 (Hojeibane), EP 0 956 832 (Richter et al.), PCT/US98/08194 (Dubrull).

An endolumenal prosthesis has to fulfil two somewhat conflicting requirements.

First of all, the endolumenal prosthesis has to have a high degree of flexibility when it is in its non-expanded state to facilitate the delivery of the prosthesis through the tortuous anatomy as far as the implantation site. Moreover, when the prosthesis is in the expanded condition, it has to demonstrate sufficient radial stiffness to minimize the collapse of the walls of the duct in which it has been deposited and, for example, re-stenosis effects, as well as effectively resisting the possibility of acute occlusion. These conflicting requirements, that is, the provision of a prosthesis which has considerable flexibility when in the non-expanded condition whilst having great radial stiffness in the expanded condition, have been achieved in the past with the use of struts that are interconnected, typically with a longitudinal arrangement, to confer great flexibility on the prosthesis in the non-expanded or contracted condition, and further interconnected struts, for example, nonlongitudinal circumferential lines or rings of struts, which open up to rings that are stiff radially (at least in an ideal situation), to confer the necessary radial stiffness on the prosthesis in expanded conditions.

A solution which partially satisfied these requirements was proposed in US patent application 2002/0065547 (Moore).

There is nevertheless still a further great need to find an endolumenal prosthesis which can easily be clenched in a radially contracted position around delivery and expansion devices (SDS). This need in fact conflicts particularly with the need to have interconnected circumferential struts that are capable of withstanding radial stresses adequately when in the expanded condition. In fact these struts are difficult to clench around the delivery and expansion devices (SDS) precisely because of their structural capacities.

SUMMARY OF THE INVENTION

The problem underlying the present invention is therefore that of proposing an endolumenal prosthesis which has structural and functional characteristics such as to overcome the disadvantages of the prior art in order to satisfy the above-mentioned requirements.

This problem is solved by means of an endolumenal prosthesis of the type described in claim 1.

BRIEF DESCRIPTION OF THE DRAWINGS

Further characteristics and the advantages of the endolumenal prosthesis according to the invention will become clear from the following description of the preferred embodiments thereof which are given purely by way of non-limiting example with reference to the appended drawings, in which:

FIG. 2 shows a detail relating to a line portion of the pattern of FIG. 1, FIG. 3 shows a detail relating to a module of the line of FIG. 2, FIG. 4 shows a further detail of the line of FIG. 2, relating to a further module, FIG. 4*bis* shows a lobe according to a further embodiment, FIG. 15 shows a cell relating to a further portion of the pattern of FIG. 14, FIG. 16 shows a cell of a portion of the pattern of FIG. 14, FIG. 17 shows a cell of a portion of the pattern of FIG. 14, FIG. 18 shows a cell of a further portion of the pattern of FIG. 14.

DETAILED DESCRIPTION OF INVENTION

The term "porous wall" is used below to indicate the wall of an endolumenal prosthesis comprising a pathway or a plurality of interconnected or interlaced pathways which form loops or "struts" of a network delimiting apertures or cells.

Figure 1:
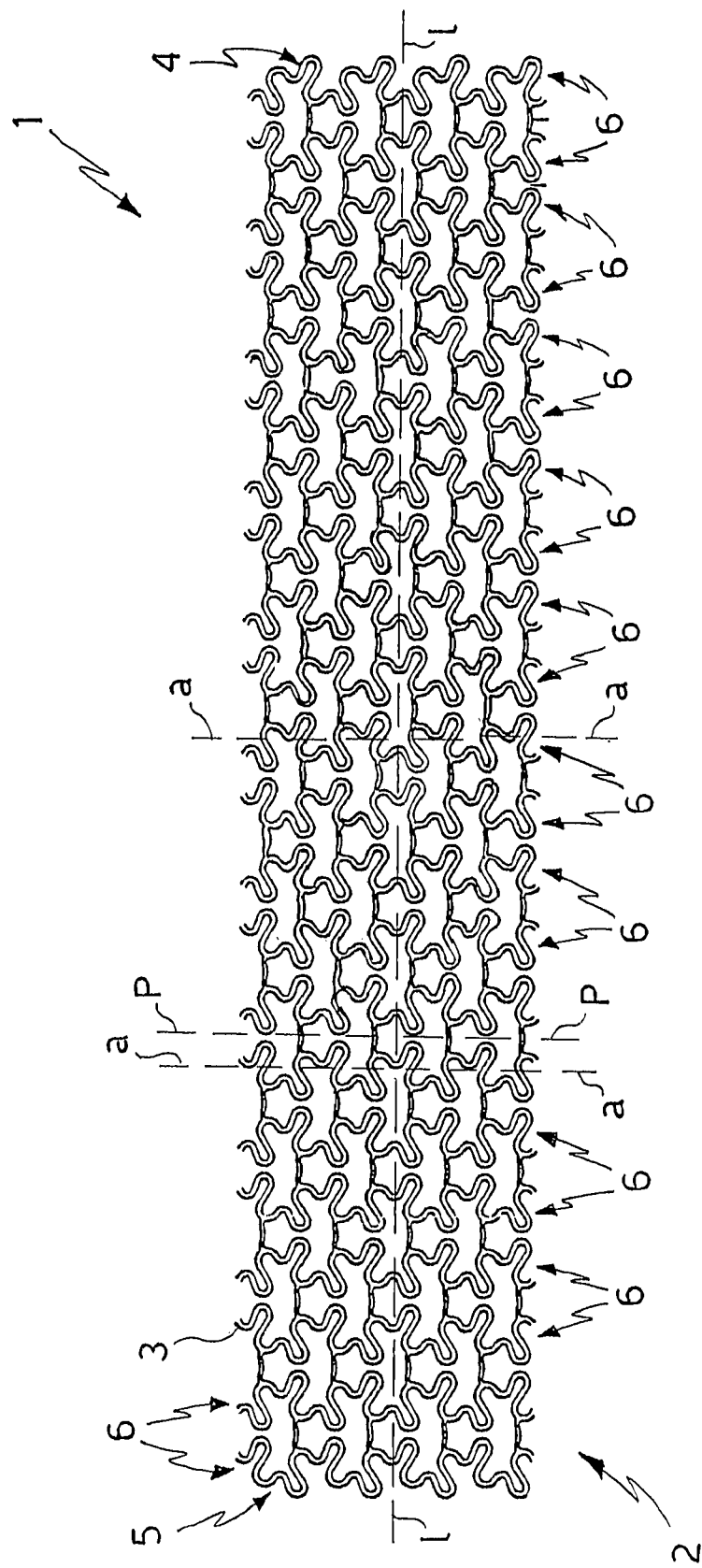
FIG. 1 is a two-dimensional view of a pathway motif or pattern for an endolumenal prosthesis, in the non-expanded configuration.

The term "pattern" indicates the pathway motif of the wall of an endolumenal prosthesis. Preferably, the pathway motif forming the pattern is shown, for convenience, as a flat surface, for example, as illustrated in FIG. 1, rather than with a tubular geometrical shape.

The term "line" means a portion of the pattern formed by a continuous pathway which extends, following a predetermined pattern, for example, in a substantially circumferential or helical direction, forming a "circumferential line".

The term "axis of a line" means a substantially median line of the extent of a continuous pathway forming a line.

The term "interlaced" (or interconnected) means that a portion of a continuous pathway is connected to or shared with other continuous pathways extending in the same or a different direction.

The term "lobe" means a section of the pathway of curved shape, or even a plurality of curved sections which are joined to one another or are connected by means of straight sections and the concavities of which have the same orientation. In a lobe, the inclination or orientation of the line tangential to the pathway changes.

"Apex of a lobe" means a reference point of the lobe, for example, the point of the pathway forming the lobe which is disposed farthest from the axis of a line.

"Distance between apexes" means the distance, measured on a straight line perpendicular to two parallel and tangential straight lines each extending through the apex of a lobe.

"Aperture of a lobe" means the area that is surrounded by the pathway forming a lobe or that is inside the curved portion.

"Arm" indicates a single straight section formed by a portion of the continuous pathway which is not interrupted by curved sections or lobes. In particular "arm" means a straight portion of pathway having an extent greater than that of a joining point between two curved portions or sections.

"Module" means a portion of the continuous pathway, for example, of a line and, in particular, of a circumferential line, which has a motif that is repeated in the pattern either identically or as an identical mirror image, even though with pathway sections or portions that are common to several modules. According to one embodiment, each module comprises three lobes which are formed in series in a portion or section of pathway and are joined by their outer portions to straight sections or outer arms. If the motif of the module is arranged with the outer arms extending downwards, away from the outer lobes, the motif is substantially M-shaped with a joined or rounded section.

"Cell" means the area enclosed by a closed pathway, for example, formed by sections of lines and bridges which connect the lines. The closed pathway delimits an opening in the wall of the body of the endolumenal prosthesis.

"Non-expanded configuration", "non-expanded condition", or "non-expanded position" mean the configuration of the tubular body of the endolumenal prosthesis in the dimensions in which it is produced, for example, by laser cutting from a piece of tube of predefined length, predefined outside diameter, and predefined wall thickness. The cylindrical wall of the tubular body is shown opened out in plan in order to illustrate the geometry or pathway motif of the prosthesis.

"Clenched configuration" or "crimped configuration" means the configuration or arrangement of the tubular body of the prosthesis to which it is contracted radially by moving bent or inclined sections of the circumferential lines towards one another, for example, in order to bring the wall of the tubular body into contact with a device for the delivery and expansion of the prosthesis.

"Expanded configuration" means the configuration or arrangement of the tubular body of the prosthesis to which it is enlarged radially so as to move the bent or inclined sections of the circumferential lines apart to constitute support elements, for example, suitable for supporting previously collapsed duct walls in the expanded position, or suitable for restoring a predefined bore of a lumen for the correct passage of a fluid.

"SDS" means Stent Delivery System or a device for delivering the endolumenal prosthesis and expanding it in situ. For example, an SDS is a catheter provided, at a distal end, with a balloon which, when deflated and in the folded position, can support the prosthesis in the clenched configuration and, when inflated, can bring the prosthesis to the expanded configuration. Examples of SDS devices are given, for example, in the documents VR1995A000089 (SHEIBAN) and PCT/EP00/12964 (LOALDI), which are included herein by reference, in particular, with regard to their description of the SDS.

With reference to the above-mentioned drawings, a pattern as a whole, defined by the wall of a tubular body of an expandable endolumenal prosthesis 2, is generally indicated 1. The pattern is shown flat as though the wall of the prosthesis had been cut longitudinally and unrolled when in the non-expanded configuration.

Advantageously, the expandable endolumenal prosthesis 2 comprises, in the non-expanded configuration, the body 3, for example, of tubular shape, which extends along a longitudinal axis 1-1 and has a distal end 4 and a proximal end 5.

The tubular body comprises a porous wall which is defined by a plurality of circumferential lines 6 connected to one another or interlaced or interconnected to form the pattern or pathway motif (FIG. 2).

Advantageously, at least one line 6 of the plurality of lines is closed onto itself, meaning that, when the longitudinal edges of the unrolled pattern are made to coincide, the continuous pathway which forms this line is closed onto itself. Each of the lines 6 extends along an axis or line axis a-a. For simplicity, only two of these are shown in FIG. 1.

Each of the lines 6 comprises at least one plurality of modules 7 (FIGS. 3 and 4). According to one embodiment, at least one line 6 comprises two pluralities of modules 7 which have identical geometry but are mirror images of one another with respect to an axis, for example, an axis parallel to the axis a-a of the line 6. Modules that are identical mirror images are considered below as a single plurality of modules.

Each module 7 comprises three lobes 8 and 9, that is, two outer lobes 8 and one inner lobe 9 disposed between the two outer lobes 8 in the pathway of the pattern (FIGS. 2, 3 and 4).

Advantageously, each lobe 8, 9 comprises one or more curved sections 10 which have their concavities facing in the same direction and, for example, are joined together by a straight section 11. Each lobe defines a lobe apex. The lobe apex is a reference point of the lobe identifiable, for example, by means of a line tangential to the lobe and parallel to the axis of the line.

Advantageously, the lobes 8, 9 open alternately on opposite sides of the pathway of the pattern, along the line 6, as indicated by the arrows 14 in FIG. 2.

With further advantage, both of the outer lobes 8 of the three lobes are extended by straight outer arms 15.

The at least one plurality of modules 7 are arranged consecutively so as to have successive outer arms 15 which extend from the outer lobes 8 in substantially opposite directions relative to the pathway of the pattern, for two successive modules.

With particular advantage, for each module 7, the distance d1 between the apex 13 of one of the outer lobes 8 and the apex 13 of the inner lobe 9 of the same module is less than the distance D2 or D3 between the apex 13 of the same outer lobe 8 and the apex of any outer lobe of an adjoining module (FIG. 2).

According to one embodiment, the inner lobe 9 of at least one module 7 is extended by at least one straight inner arm 16.

According to a further embodiment, both of the ends of the inner lobe 9 are extended by straight arms 16 (FIGS. 16, 17, 32, 33 and 35).

Advantageously, at least one of the outer arms 15 extends along an axis which is inclined to the longitudinal axis 1-1 of the tubular body 3 and is also inclined to the axis a-a of the line to which the module belongs. For example, the outer arms 15 are inclined to the longitudinal axis 1-1 of the prosthesis so as to be substantially approximately offset slightly from a direction parallel to the axis 1-1 when the prosthesis is in a clenched configuration. It is thus much easier to close up or clench the prosthesis radially, for example, around a delivery and expansion device (SDS). In fact, it is surprisingly easy to deform the module in a direction that is substantially transverse or slightly offset from the direction transverse the straight arms 15 when the prosthesis is in the non-expanded configuration (FIG. 2).

According to one embodiment, both of the outer arms 15 of the module 7 extend along an axis R-R which is inclined to the longitudinal axis 1-1 of the tubular body 3 and is also inclined to the axis a-a of the line to which the module belongs.

With particular advantage, the outer arms 15 of the module 7 extend away from the lobes 8 along converging axes R-R. For example, the axes R-R of the outer arms of a module include an angle A of between 5 and 85 degrees (FIGS. 3 and 4). Advantageously the angle A is between 10 and 80 degrees and preferably between 30 and 70 degrees.

According to one embodiment, the inclination of the axis R-R of the outer arms is substantially close to the direction transverse the longitudinal axis 1-1 of the prosthesis when the prosthesis is in the expanded configuration. The outer arms thus act as struts of a support framework for the wall, for example, of the vessel in which the prosthesis is implanted.

Advantageously, at least one outer arm 15 or, for example, both of the outer arms of a module 7, are shared with a module adjacent thereto.

According to one embodiment, the outer arms 15 of the module 7 are of equal extent.

In an advantageous embodiment, the inner lobe 9 is joined to outer lobes by means of at least one inner arm 16.

In a particular embodiment, the inner lobe 9 is extended at both ends by two straight inner arms 16, for example, of equal extent.

In its overall shape, in each module, the overall extent of the inner lobe together with its inner arm or inner arms is advantageously less than the overall extent of each outer lobe together with its outer arm. According to a further embodiment, the extent of the outer lobes 8 and the inner lobes 9 together with their respective outer arms 15 or inner arms 16 in a direction transverse the axis a-a of the line, is non-uniform.

Figure 14:
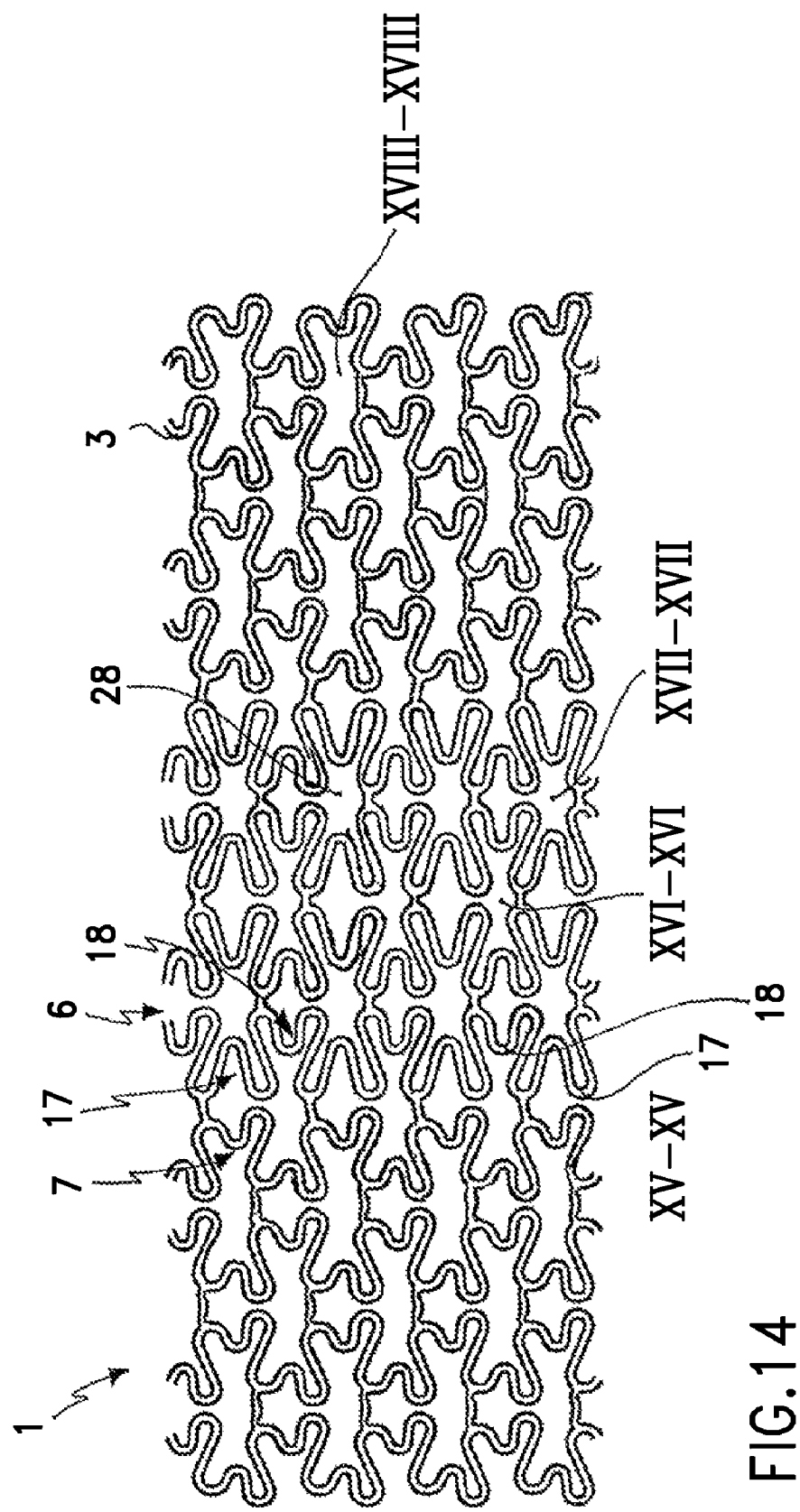
FIG. 14 is a two-dimensional view of the motif or pattern relating to an endolumenal prosthesis according to a further embodiment.
Figure 19:
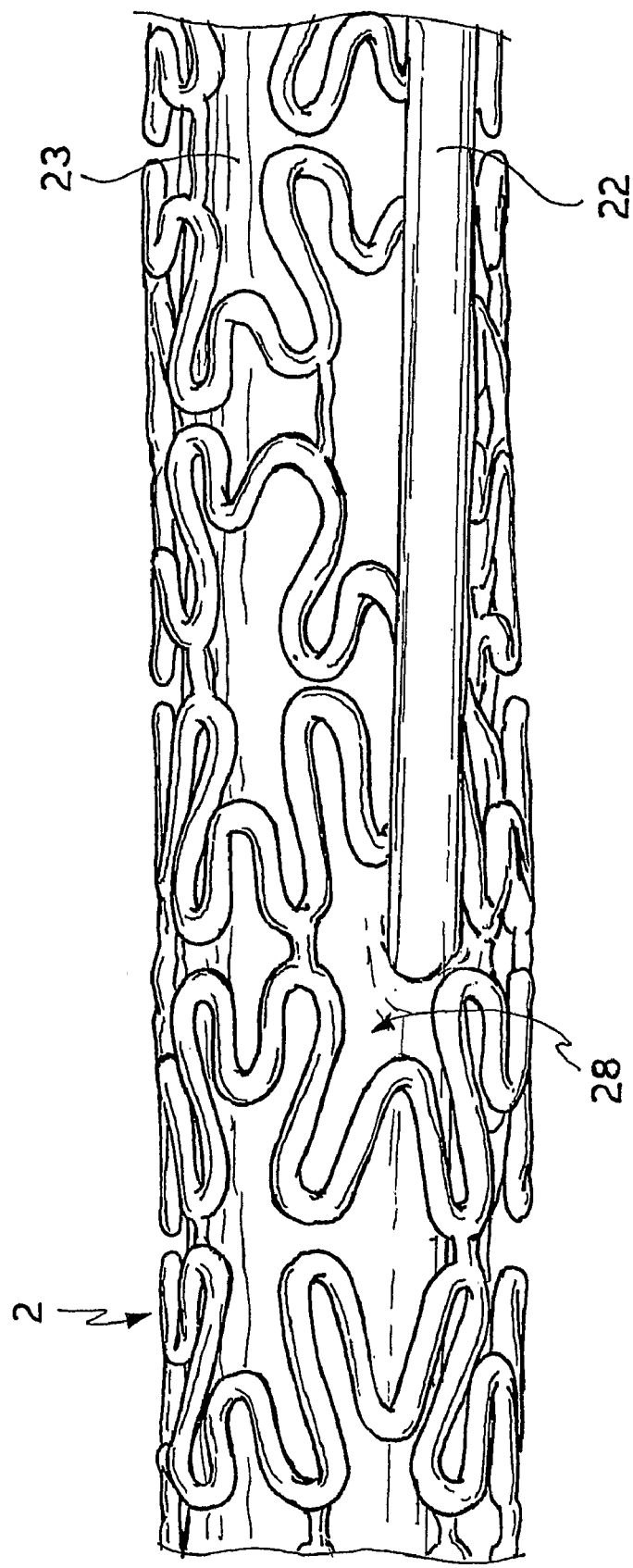
FIG. 19 is a prospective view of a portion of the prosthesis according to the pattern of FIG. 14, clenched around a portion of an SDS.
Figure 20:
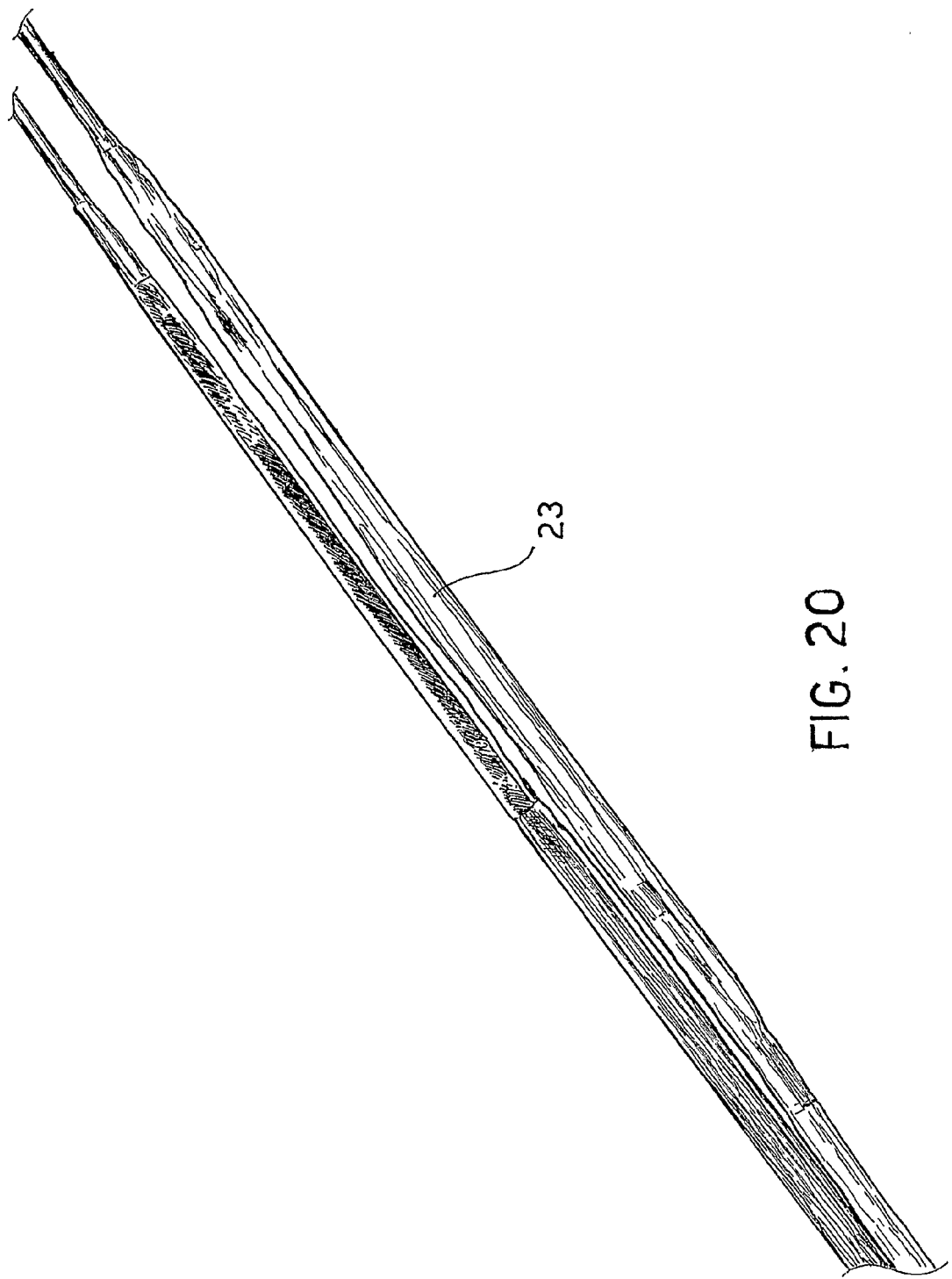
FIG. 20 shows a distal portion of an SDS suitable for delivering and expanding a stent according to the invention.
Figure 21:
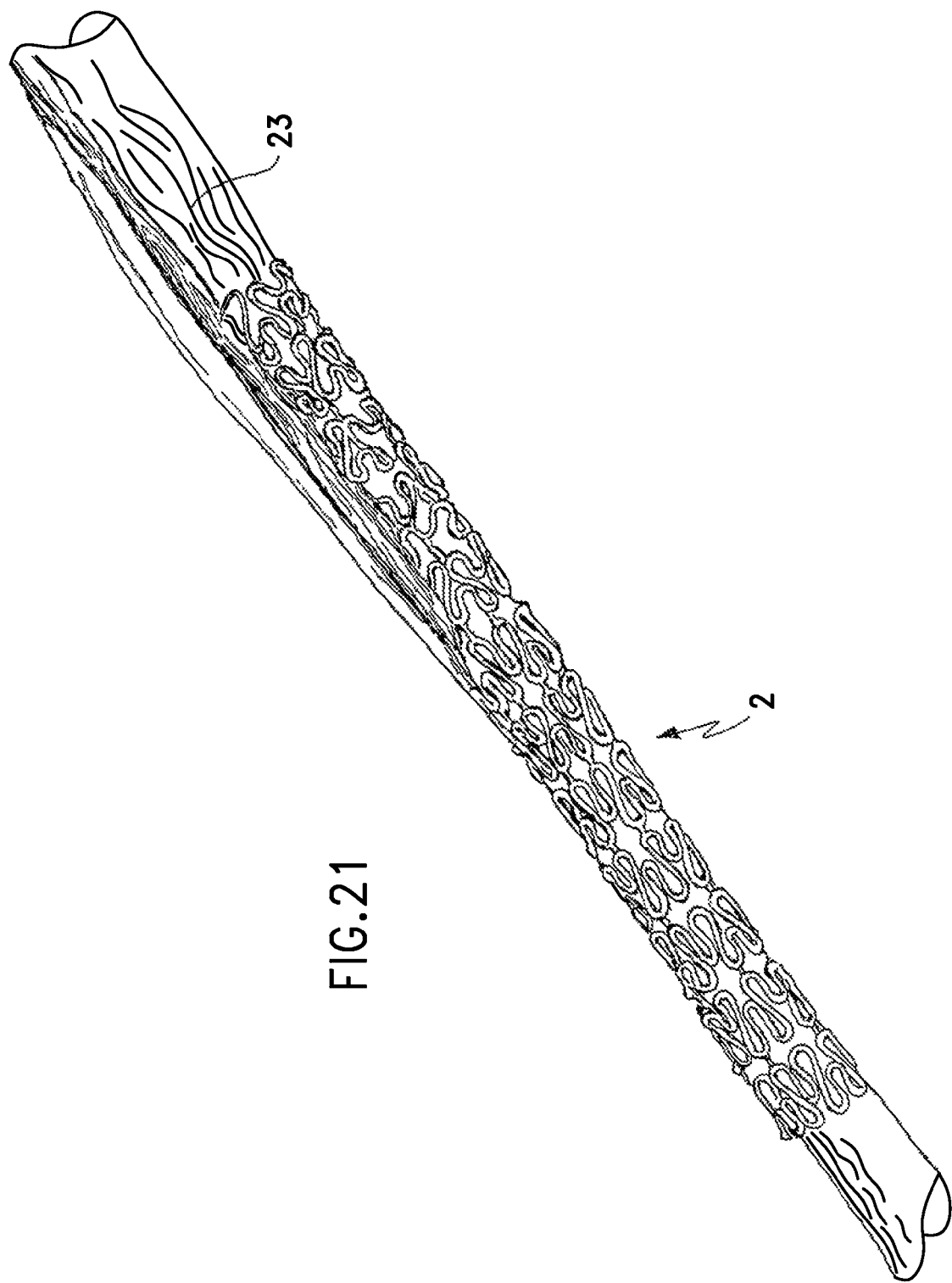
FIG. 21 is a prospective view of a distal portion of the SDS of FIG. 20 on which an endolumenal prosthesis having a pattern according to FIG. 14 is fitted in a clenched condition.
Figure 22:
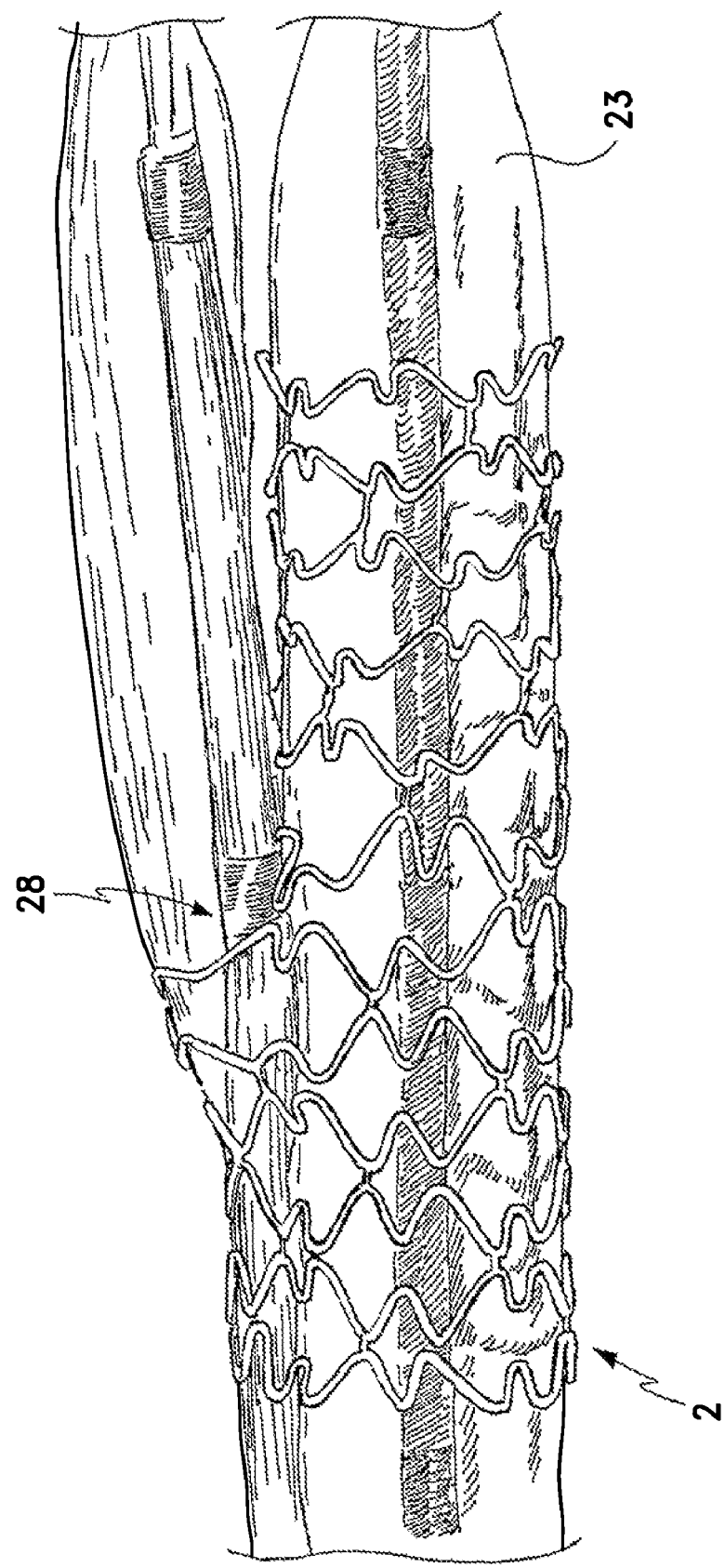
FIG. 22 is a prospective view of a portion of the SDS of FIG. 21 in the expanded configuration.
Figure 23:
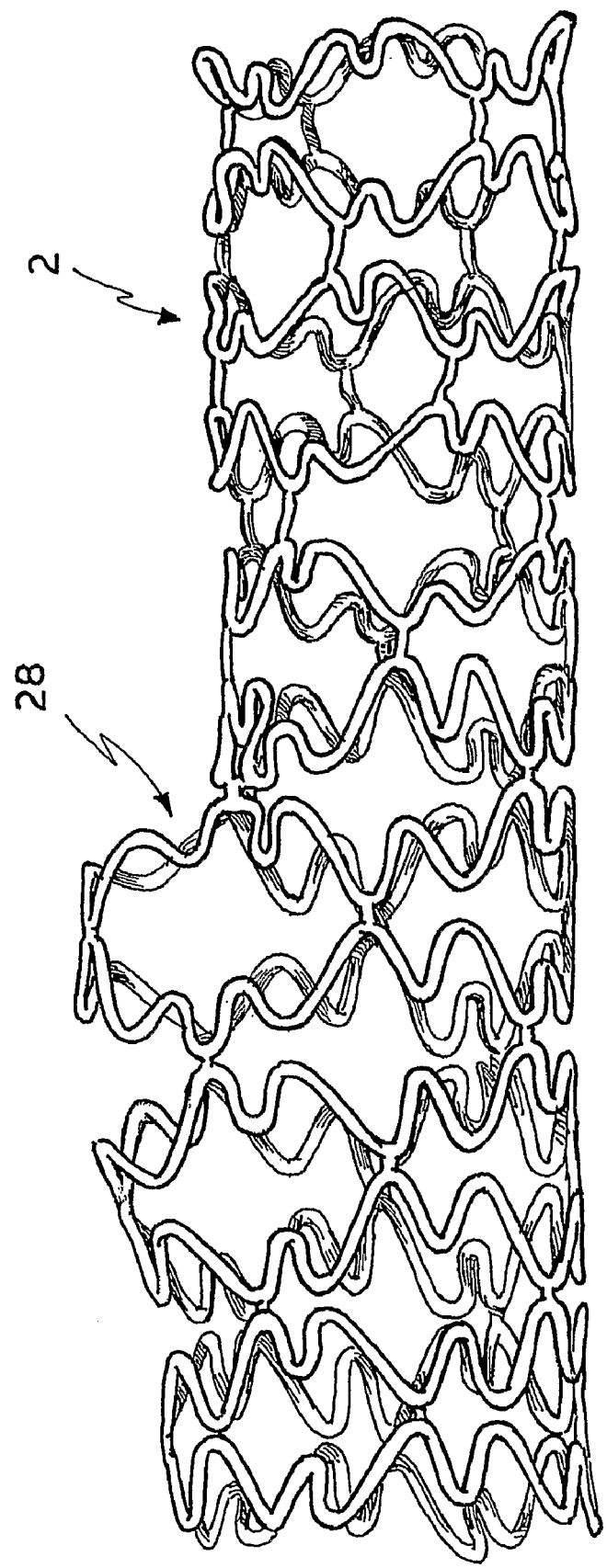
FIG. 23 shows the expanded endolumenal prosthesis of FIG. 22.
Figure 24:
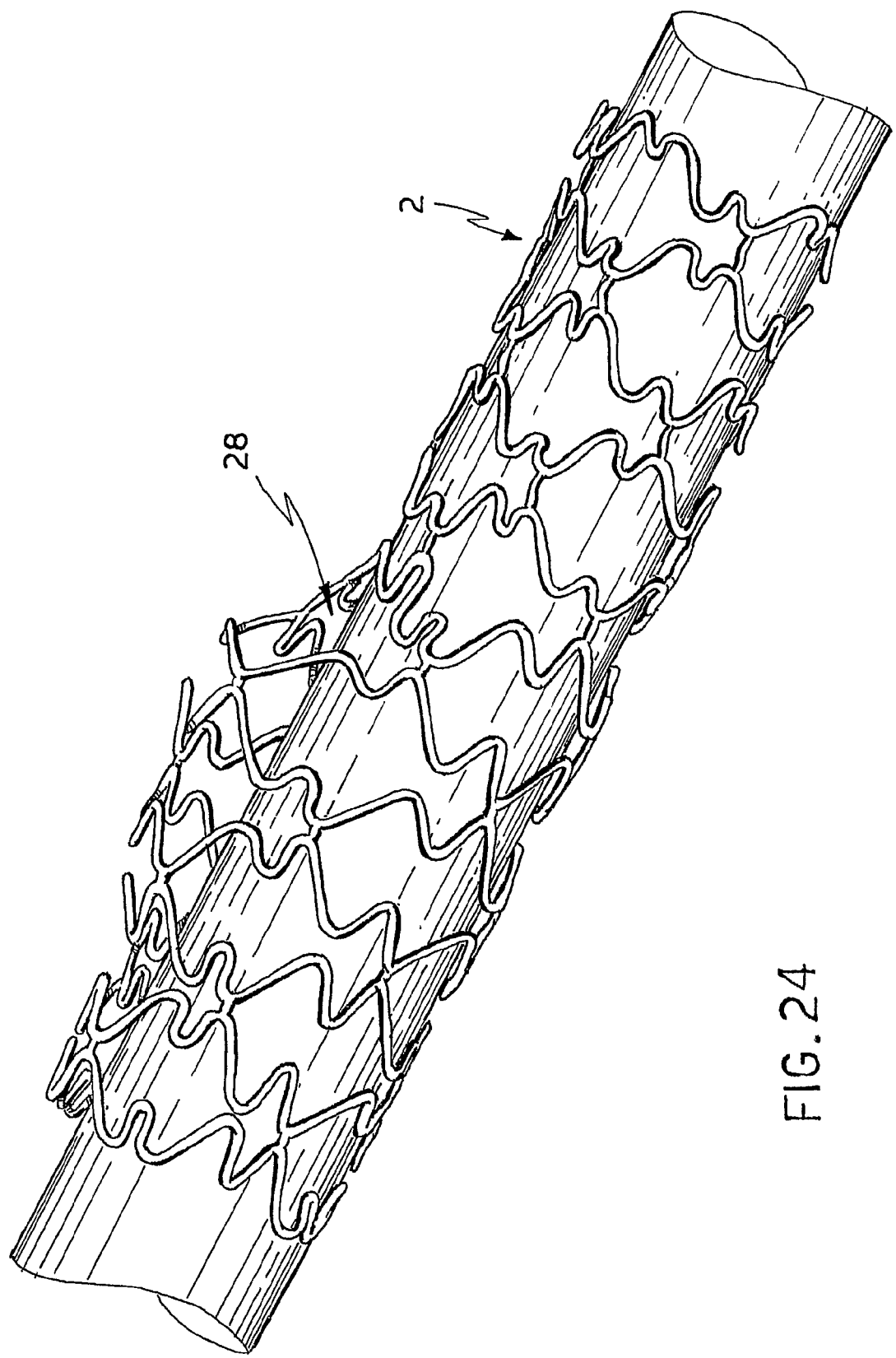
FIG. 24 is a prospective view of the endolumenal prosthesis of FIG. 23 in which a cylindrical rod is inserted to show its struts better.
Figure 25:
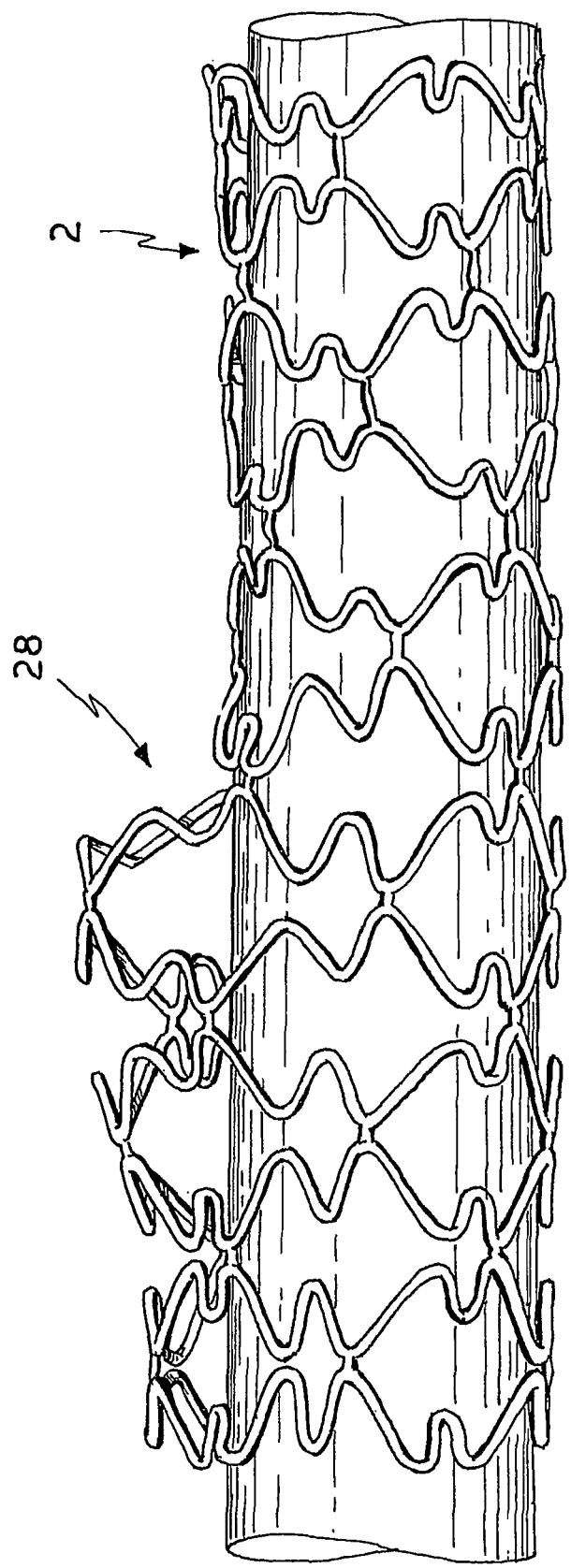
FIG. 25 shows the endolumenal prosthesis of FIG. 24 in a side view.
Figure 26:
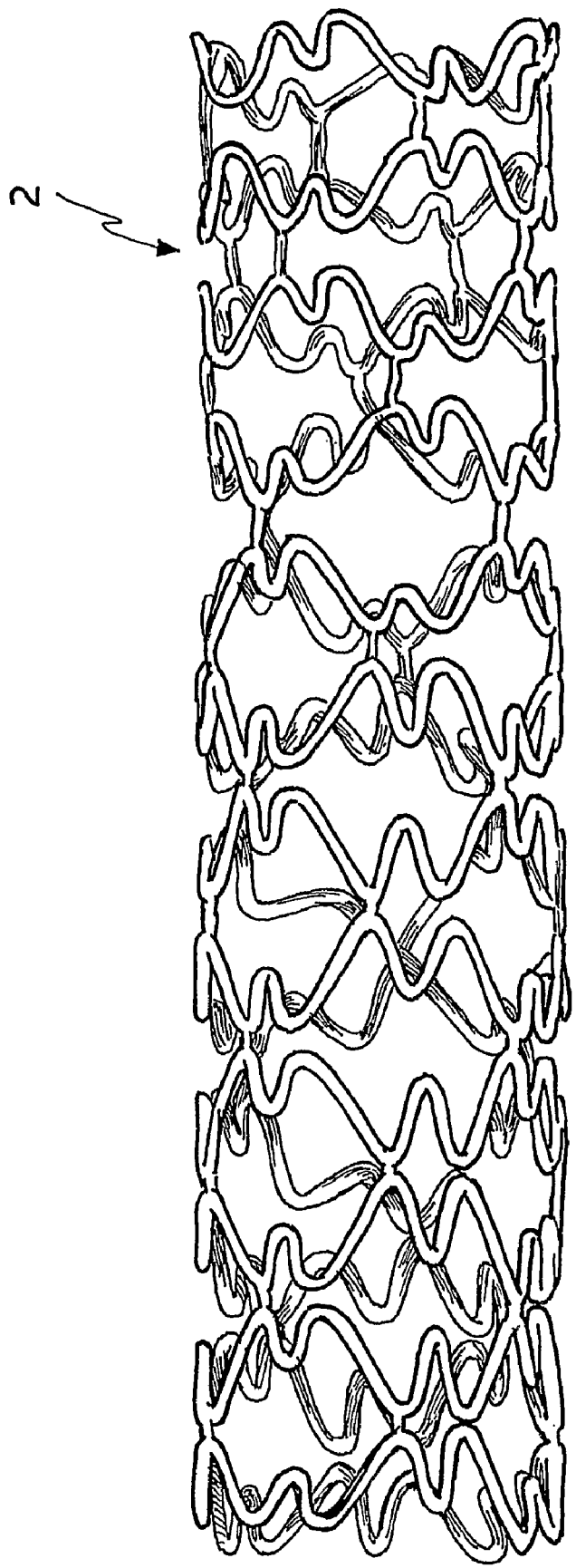
FIG. 26 shows the endolumenal prosthesis of FIG. 23 from below.
Figure 27:
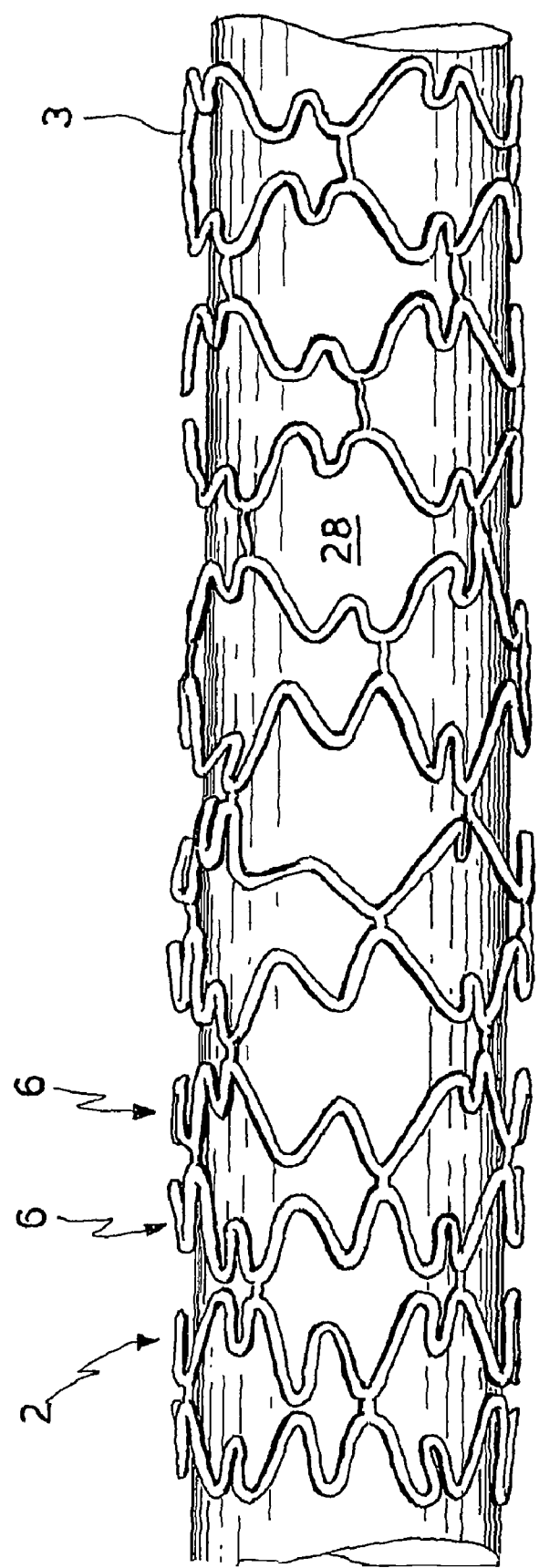
FIG. 27 shows the endolumenal prosthesis of FIG. 24 from below.
Figure 28:
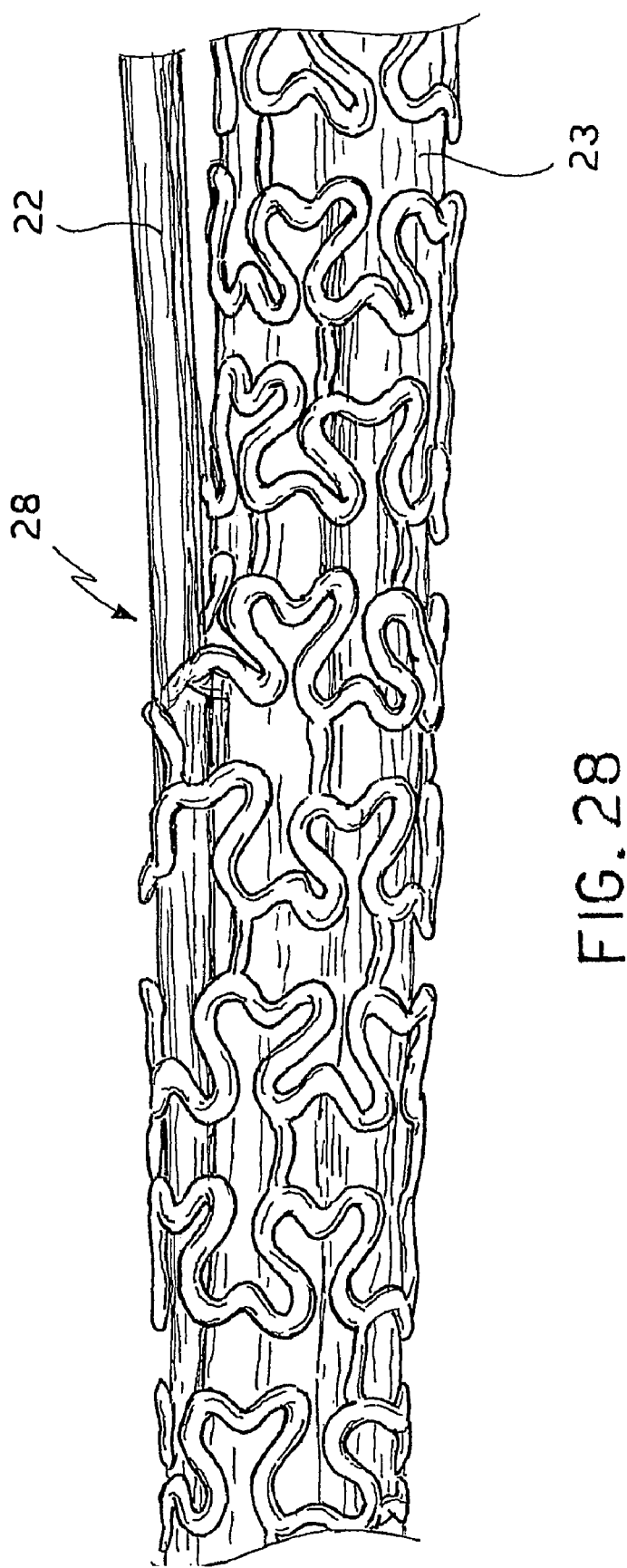
FIG. 28 shows a distal portion of an SDS provided with a lateral opening in the region of expansion means on which an endolumenal prosthesis according to the invention is fitted.
Figure 29:
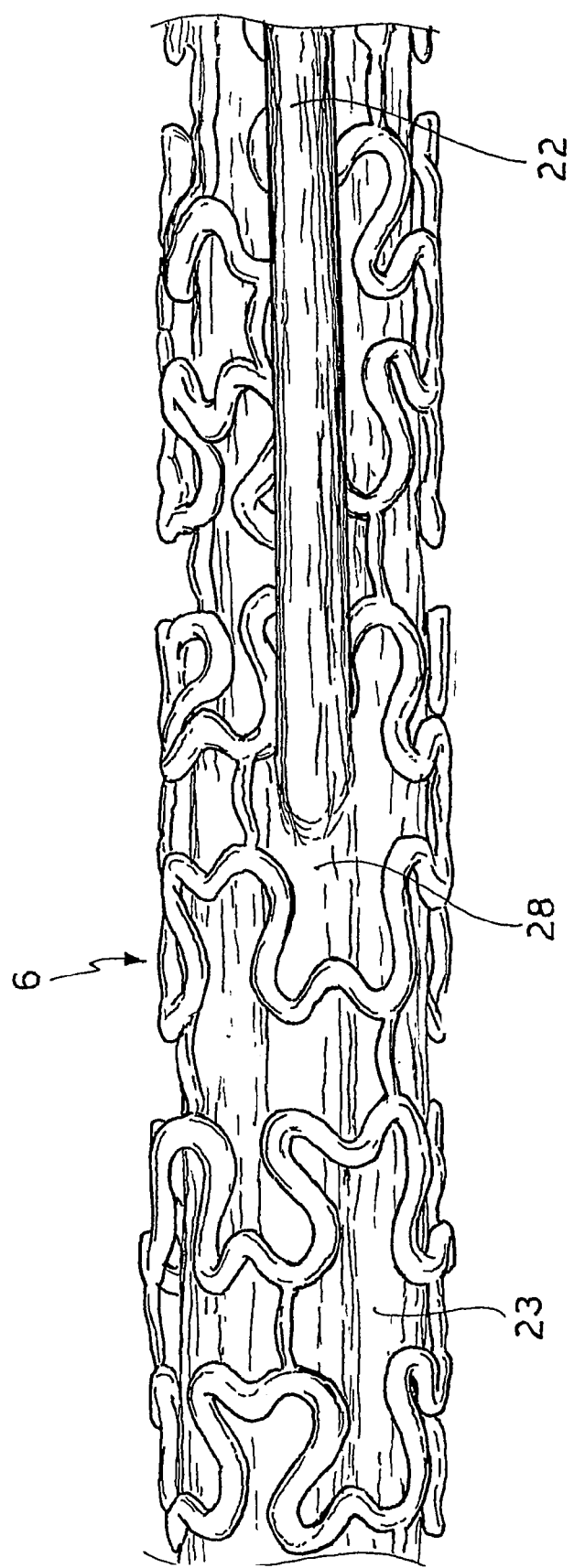
FIG. 29 shows the SDS of FIG. 28 from above.
Figure 30:
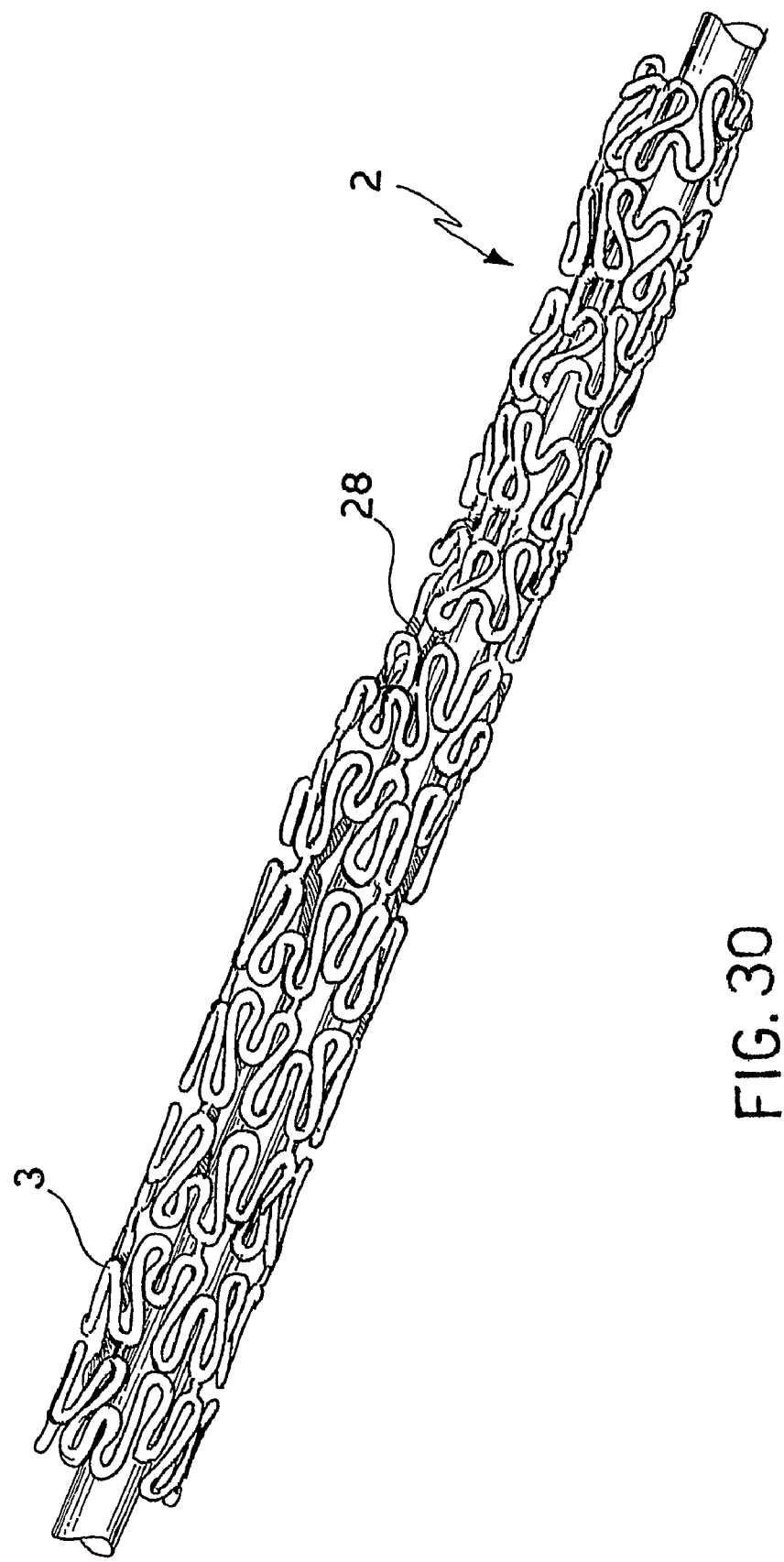
FIG. 30 is a prospective view of an endolumenal prosthesis according to the invention in the clenched position, in which a cylindrical rod is inserted to show its struts better.
Figure 31:
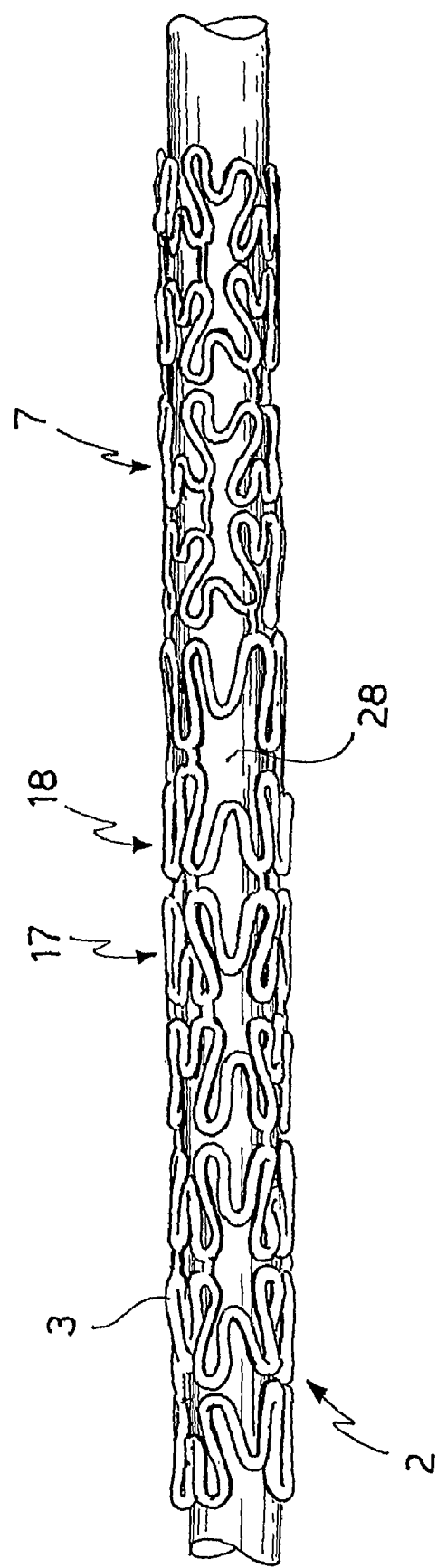
FIG. 31 shows the prosthesis of FIG. 30 from below.
Figure 34:
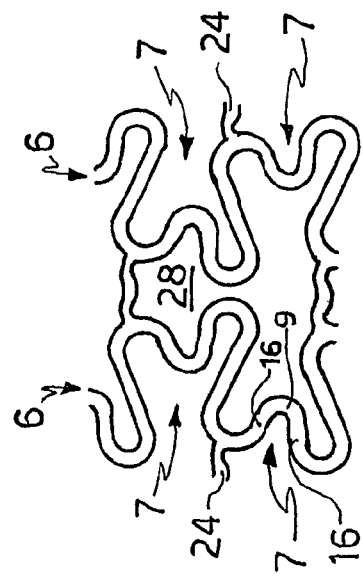
FIGS. 32 to FIG. 35 show four cells formed by means of patterns according to further embodiments.
Figure 35:
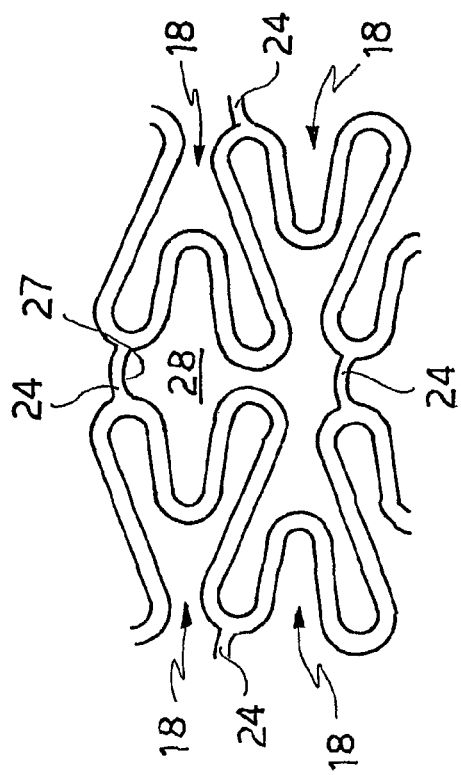
Figure 32:
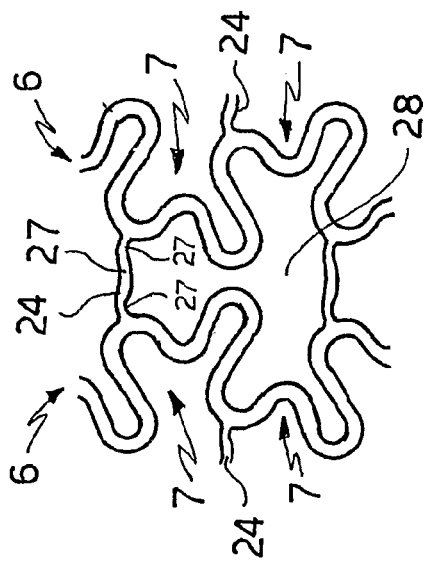
Figure 33:
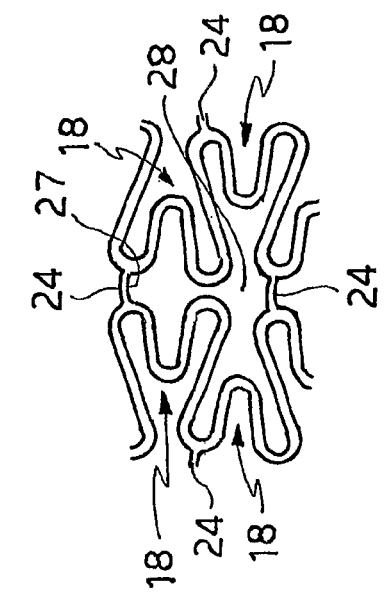

Advantageously, the extent of the outer arms 15 or of the inner arms 16 varies between modules 7 of the same line 6 or of different lines. According to a particular embodiment, the extent of the outer arms 15 or of the inner arms 16 varies in the modules from one line 6 to another along the longitudinal axis 1-1 of the tubular body of the prosthesis (FIG. 14).

According to further embodiments, the outer arms 15 of the same module 7 have different extents or, advantageously, have the same extent.

According to further embodiments, the inner arms 16 of the same module 7 have different extents or, for example, the same extent and, alternatively, there is only one inner arm and the opposite end of the inner lobe 9 is joined directly to the adjoining outer lobe 8 simply by extending through a point or section in which the concavity is reversed.

According to one embodiment, the arc of the curved section 10 constituting a lobe 8, 9 has a different angular extent in different modules so as to modify the aperture of the cell delimited by the module. For example, the angular extent of the curved sections forming the lobes is selected so as to delimit partially, with the module, a cell with an aperture sufficient for the passage of a guide wire 22, even when the prosthesis is in the clenched configuration. According to a further embodiment, the angular extent of the curved sections forming the lobes and the extents of the respective arms are selected in a manner such as to delimit partially, with the module, a cell having an aperture sufficient not to obstruct access to a lateral branch of a duct or vessel in which the prosthesis is implanted.

According to one embodiment, the angular extent of the curved sections forming the lobes is selected in a manner such that the arms, for example, the outer arms 15, are substantially aligned with the direction of the longitudinal axis 1-1 of the prosthesis when it is in the clenched configuration.

According to a further embodiment, the angular extent of the curved sections forming the lobes is selected in a manner such that the arms, for example, the outer arms 15, are aligned substantially with a direction transverse the longitudinal axis 1-1 of the prosthesis when it is in the fully extended configuration.

According to one embodiment, at least one of the lobes 8, 9 comprises a plurality of curved portions 10, 11 with concavities having the same orientation, with at least one interposed straight portion 12 (FIG. 4*bis*).

Advantageously, the prosthesis 2 has a structure and a pattern with modules having identical characteristics, except that some of them may be arranged as mirror images of the others. In particular, for example, all of the modules 7 of a line 6 have identical characteristics, except that some of them may be arranged as mirror images of others.

According to one embodiment, in at least one line 6, at least two pluralities of modules 7 are provided, alternating with one another so as to provide a series of a module 17 of a first plurality and a module 18 of a second plurality (FIGS. 14 and 16, 17; three details shown enlarged in FIGS. 15, 16, 17 and 18, respectively, are indicated XV-XV, XVI-XVI, XVII-XVII and XVIII-XVIII in FIG. 14). Advantageously, the prosthesis has lines 6 formed by several pluralities of modules 7.

As already mentioned above, according to one embodiment, the same module 7 is provided along the pathway of at least one line 6 and is repeated in mirror-image form with respect to an axis parallel to the axis a-a of the line.

According to one embodiment, the prosthesis 2 comprises three different modules 7, 17 and 18 (FIGS. 14 and 15).

Advantageously, at least one module 7 has outer lobes 8 that are disposed at different distances D4, D5 from the axis a-a of the line 6 (FIG. 18).

Figure 7:
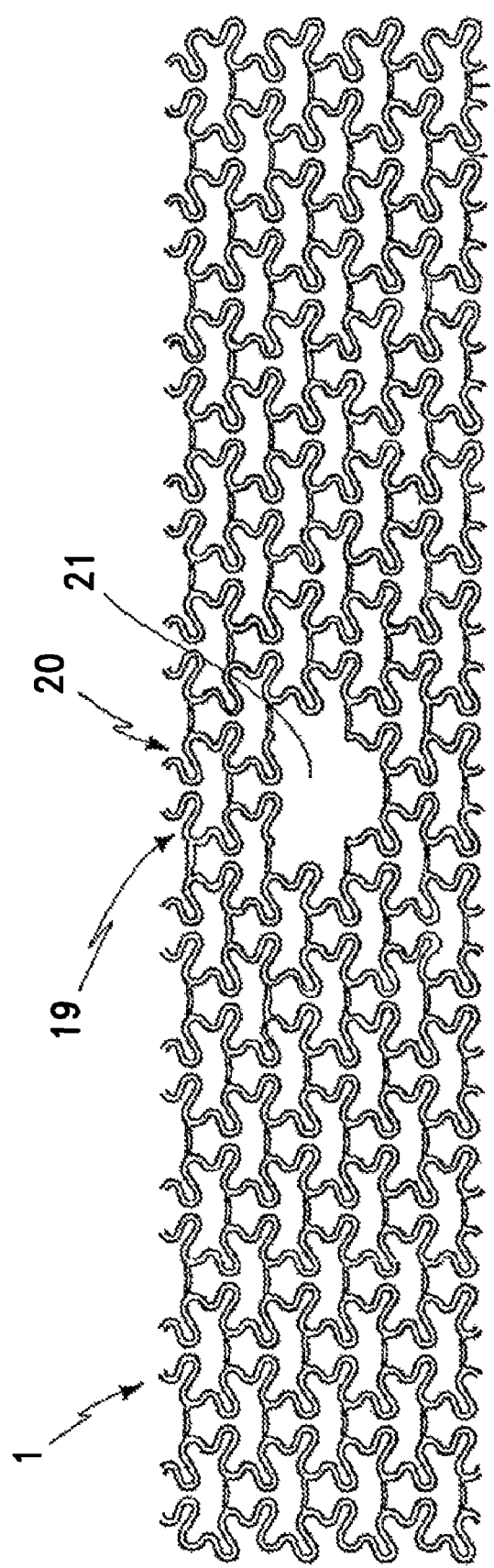
FIG. 7 is a two-dimensional view of the motif or pattern relating to an endolumenal prosthesis according to a further embodiment.
Figure 8:
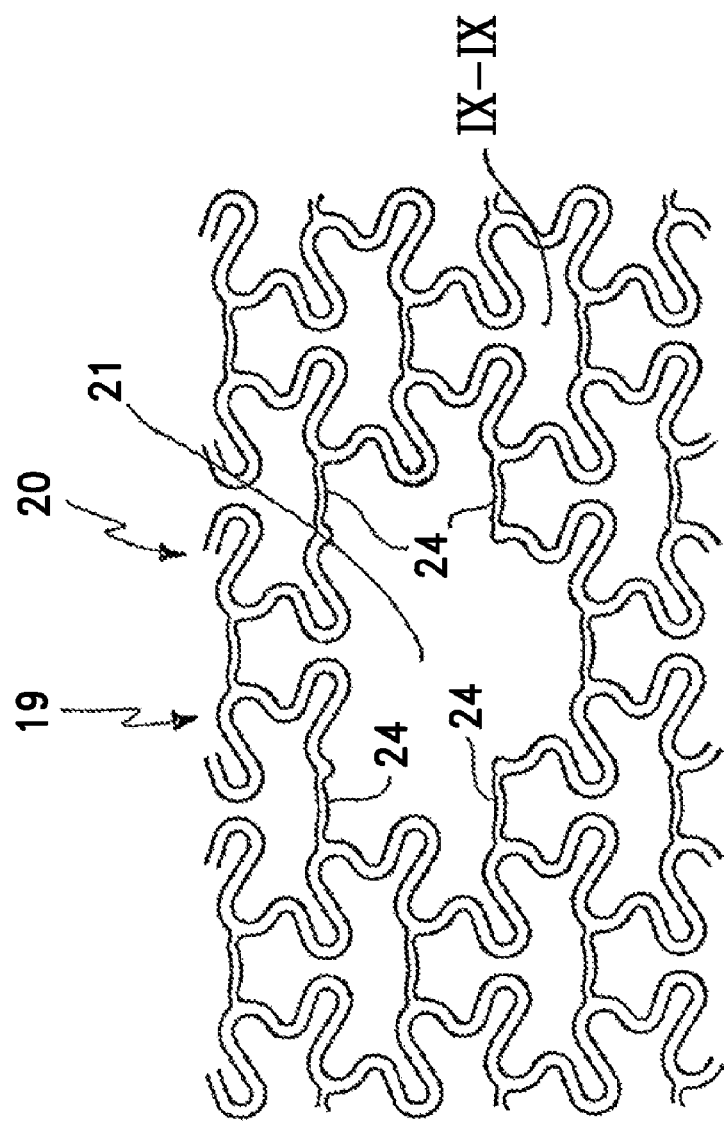
FIG. 8 shows a detail of the pattern of FIG. 7.
Figure 9:
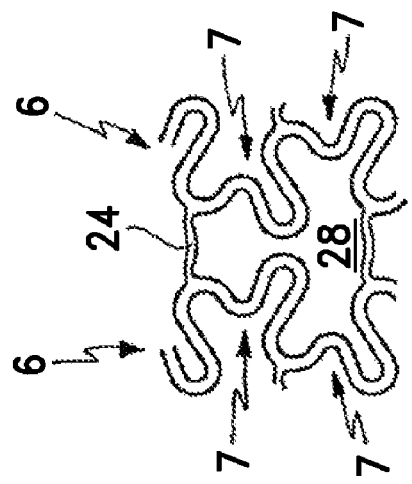
FIG. 9 shows a cell of the pattern of FIG. 7.
Figure 10:
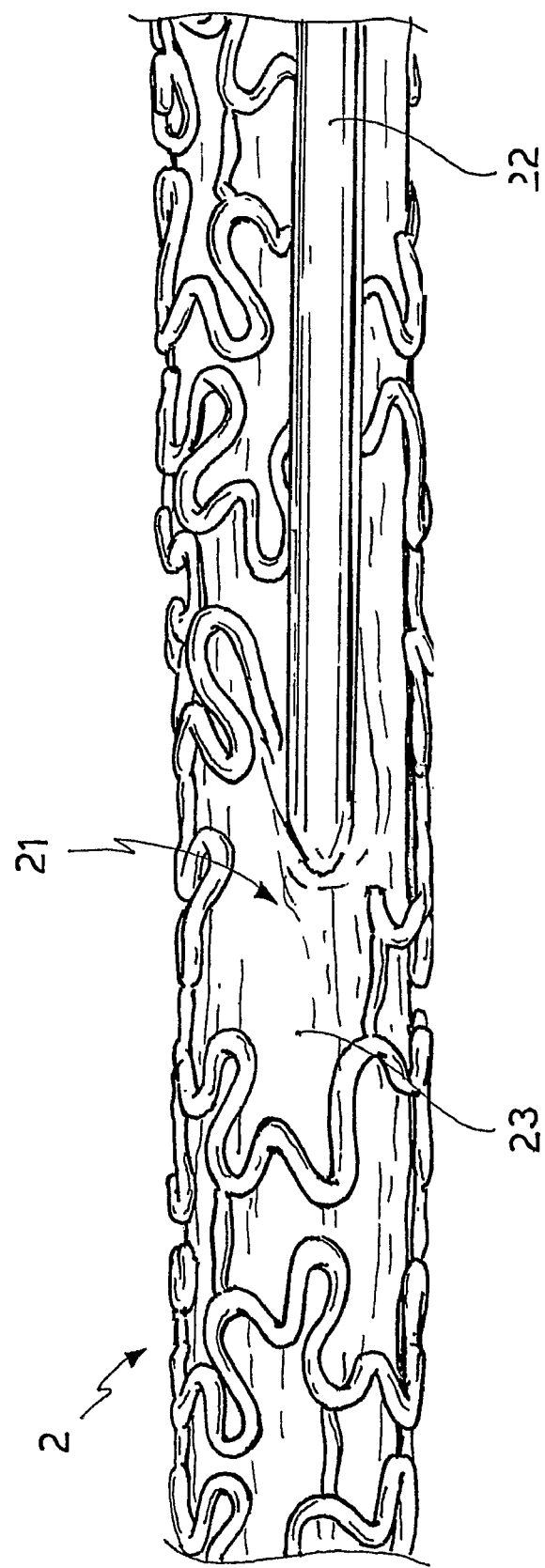
FIG. 10 shows a detail of the endolumenal prosthesis having a pattern according to FIG. 7, clenched around a distal portion of a delivery and expansion device (SDS)

According to one embodiment, in at least one line 19, 20, the pathway is interrupted so as to form an opening 21 in the pattern, for example, for the passage of a guide wire 22 for an SDS 23 (FIGS. 7, 8 and 10). For example, the pathway is interrupted to an extent equal to one module. Advantageously, the pathway is interrupted to an extent equal to five lobes, for example, consecutive lobes (FIGS. 7 and 8). Alternatively, the pathway is interrupted between two elements or bridges for connecting adjoining lines (FIG. 8). With further advantage, the pathway is interrupted in two adjacent lines 19 and 20.

Figure 11:
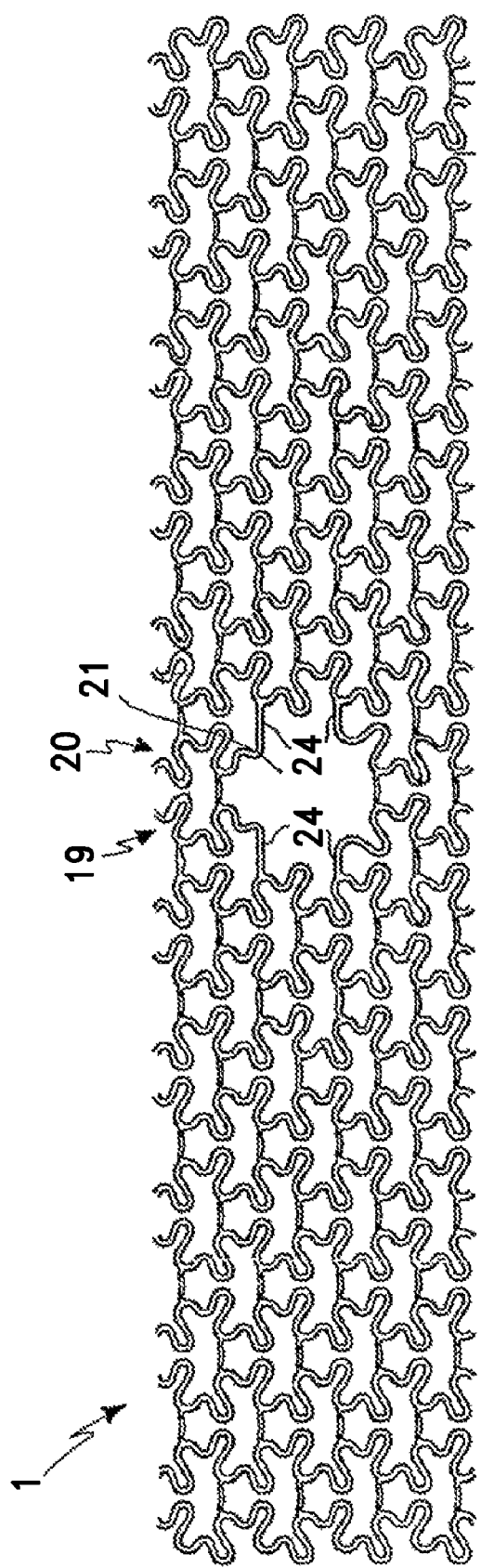
FIG. 11 is a two-dimensional view of the motif or pattern of an endolumenal prosthesis according to a further embodiment.
Figure 13:
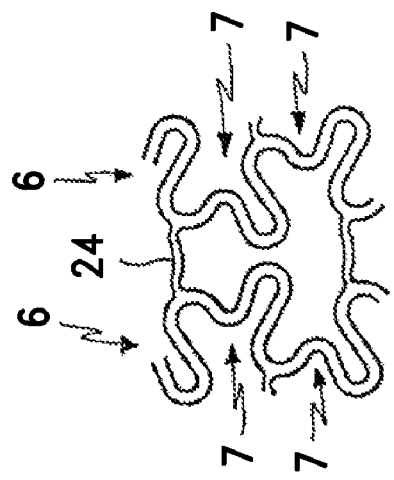
FIG. 13 shows a cell of the pattern of FIG. 11.
Figure 12:
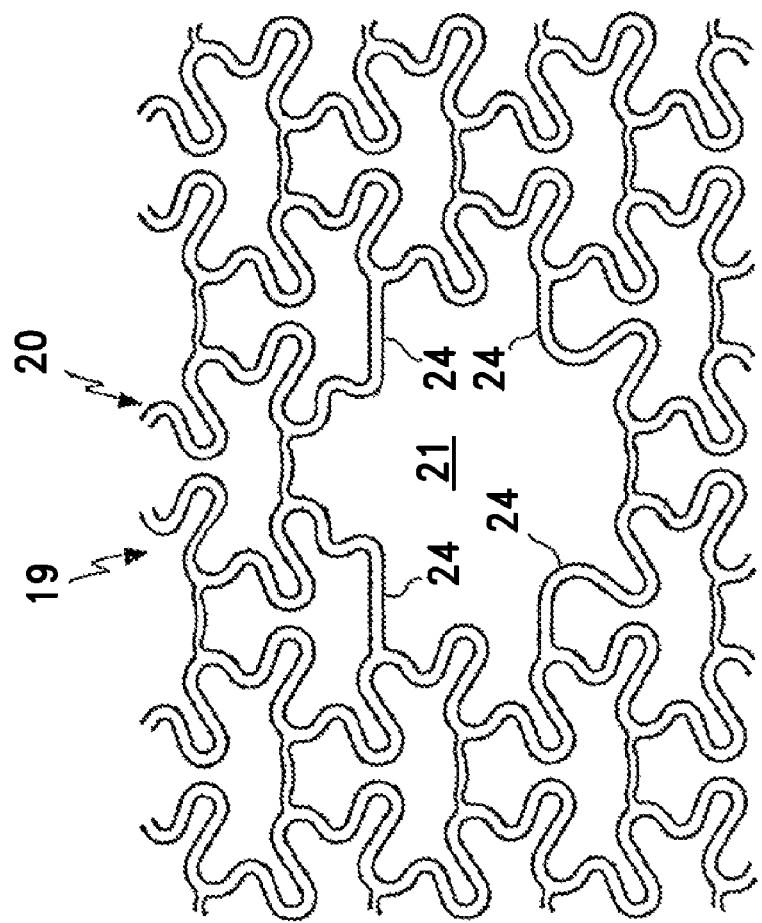
FIG. 12 shows a detail of the pattern of FIG. 11.

Advantageously, the portions of pathway of the at least one line that are close to the interruption are shaped so as to be rounded, for example, by connecting the pathway of the line to the bridges 24 (FIGS. 11 and 12).

According to one embodiment, a module 7, 17 or 18 is substantially M-shaped and is arranged so as to have outer arms directed substantially either towards the distal end 4 or towards the proximal end 5.

Figure 5:
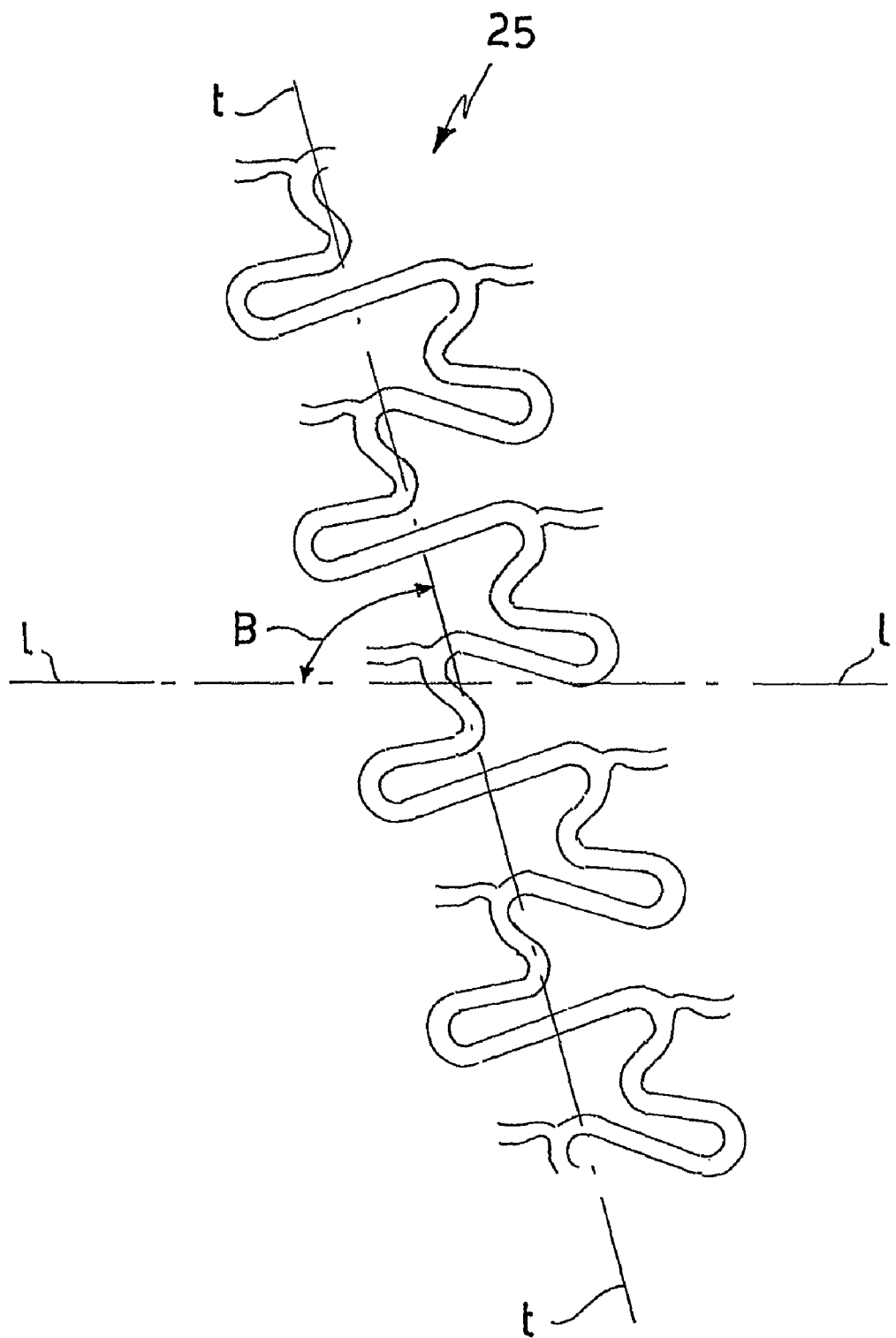
FIG. 5 shows a portion of a line according to a further embodiment.
Figure 6:
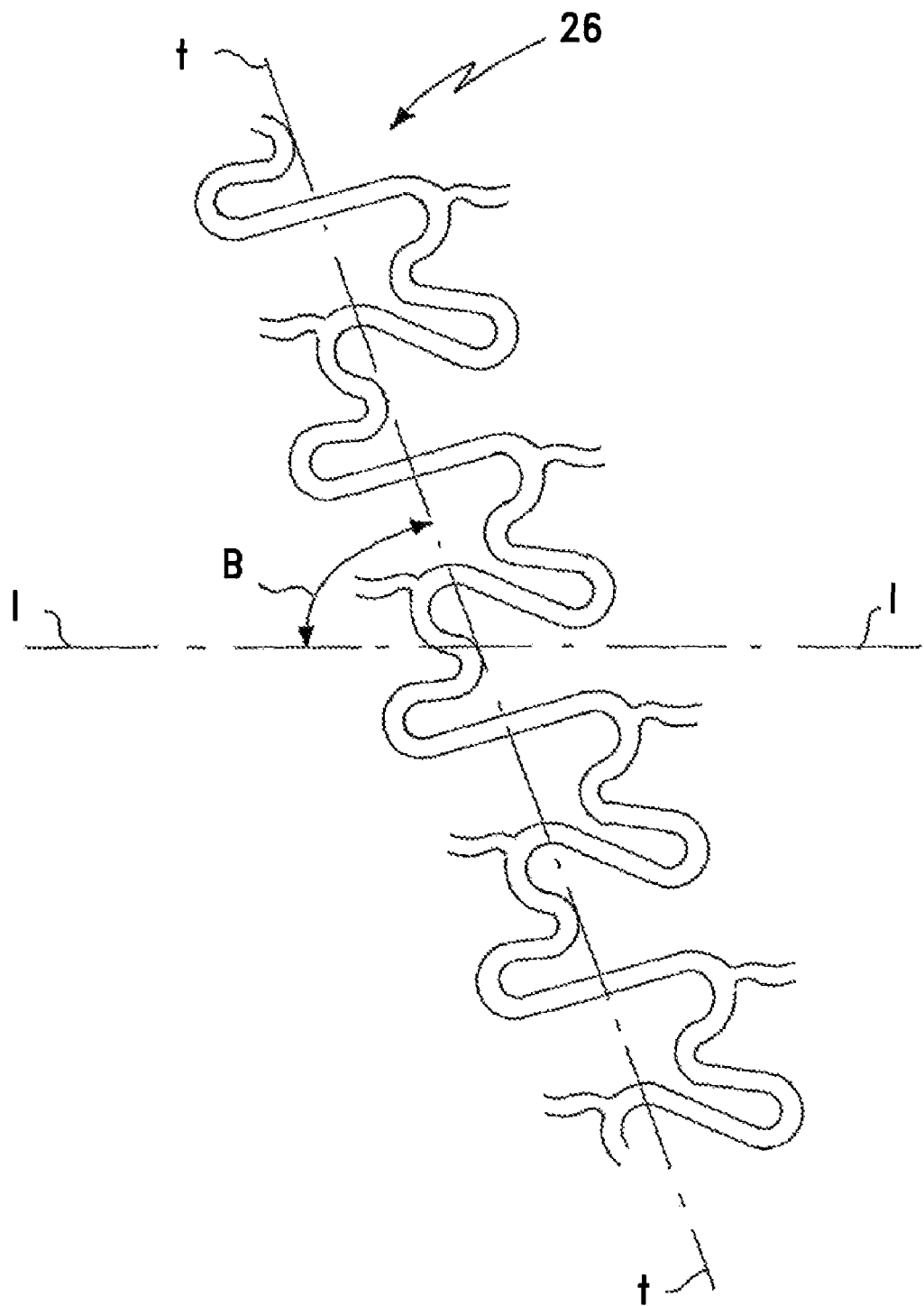
FIG. 6 shows a line portion according to yet another embodiment.

According to a further embodiment a line has its axis a-a substantially perpendicular to the longitudinal axis 1-1 of the tubular body 3. Alternatively, a line 25, 26 has an axis t-t that is inclined to the longitudinal axis 1-1 of the prosthesis 2 (FIGS. 5 and 6). For example, the axis t-t of the line 25, 26 is inclined to the longitudinal axis 1-1 at an angle B of between 5 degrees and 45 degrees and preferably between 10 and 30 degrees.

Advantageously, the axis a-a or t-t of a line 6, 19, 20, 25 and 26 is straight in the pattern, meaning circumferential in the prosthesis.

According to a further embodiment, for each line, there is at least one adjacent line, for example the adjacent line arranged in a more distal or a more proximal position than the line in question, or both of these, which adjacent line has a motif that is a mirror image of the said line with respect to an axis p-p parallel to the axis a-a of the line (FIGS. 1 and 18).

Advantageously, as already mentioned above, a connecting element or bridge 24 is provided between two adjacent lines to connect them in an interlaced or interconnected motif. For example, a bridge 24 is provided between two adjacent lines 6 for every five complete lobes 8, 9 of a line 6. Alternatively, along the line 6, a bridge 24 is provided between two adjacent lines for every first or second outer lobe 8 having the same orientation (arrow 14 of FIG. 2). Advantageously, one bridge 24 is provided per module 7, 17 or 18 and, for example, extends towards the adjacent line on the opposite side to the outer arms 15 of the module.

According to one embodiment, a bridge comprises a lobe 27 or, alternatively, a bridge comprises two lobes 27, disposed in the vicinity of the portion(s) of the bridge which is (are) joined to the pathway of the line 6. Particularly advantageously, a bridge 24 comprises three lobes 27 disposed in the region of the points of joining to the lines and in the connecting section between the two joining portions. For example, a bridge is constituted by a series of three curved sections joined to one another and having opposite concavities (FIGS. 32, 33, 34 and 35).

The closed continuous pathway comprising the sections of two adjacent lines that are included between two bridges, as well as the bridges, forms a strut delimiting a cell 28, defining a cell perimeter (FIGS. 32, 33, 34 and 35).

According to one embodiment, a variation in the perimeter of the cells present in the pattern is provided along the longitudinal axis 1-1 of the prosthesis.

A possible method for the production of the prosthesis described is described below.

According to a preferred embodiment, the starting material may be of a type that is capable of plastic deformation, for example, purely by way of indication, stainless steel, titanium, tantalum, or the like. According to a further embodiment, the starting material may be a material which expands with a memory dependent on temperature such as, for example, materials which are brought from the non-expanded configuration and in particular from the clenched or crimped configuration to the expanded configuration when a predefined temperature is reached. Purely by way of indication, these materials include materials with shape memory such as nitinol and the like.

The prosthesis of the invention described herein can be produced by various known techniques. For example, it may preferable to produce the prosthesis starting with a unitary tubular body or, in other words, a cylindrical tube with a continuous surface, and then to machine the tubular body so as to remove portions to define a porous surface, for example, by creating slots in the wall of the cylindrical tube.

Naturally, there are no restrictions on the type of process to be used to produce this porous surface and the possibility of using laser cutting machines with controlled movement operable by means of programmable numerical control is mentioned purely by way of indication.

The following may be a possible production method.
1. Providing a unitary tubular body.
2. Moving the tubular body longitudinally and rotationally beneath a laser beam so as selectively to remove portions of the wall of the solid body so as to define a porous surface.
3. Cutting the prosthesis from the remaining portion of the tubular body to a desired longitudinal length.

Purely by way of indication, a laser machine suitable for processes of this type is the LPLS-100 Series Stent Cutting Machine.

Operations of this type permit the production of a device that has resilience characteristics in this non-expanded state.

According to one embodiment, the prosthesis may subsequently be subjected to a further process for the application of a coating material. This coating material may be arranged continuously or discontinuously on the surface of the prosthesis and on the outer surface or on the inner surface of the tubular body of the prosthesis.

The coating material may be one or more of the biologically inert materials that are suitable for reducing, for example, the predisposition of the prosthesis to produce thromboses (thrombogenicity) and also a composition which releases drugs onto the walls of the duct in which the prosthesis is implanted, for example, purely by way of indication, a drug having anticoagulant properties or properties for opposing re-stenosis, or similar compositions.

The prosthesis is preferably provided with a biocompatible coating in order to minimize adverse interaction with the walls of the vessel and/or with the fluid, for example blood, which flows inside the vessel. The coating is preferably a polymeric material which is generally applied to the stent by means of a solution or dispersion of a polymer added to a solvent which is subsequently removed. Alternatively, a non-polymeric coating material may be used.

Purely by way of indication, a possible coating material may be polytetrafluoroethylene, silicone rubber, or polyurethane having known biocompatible properties. An optimal coating may be produced by the selection of coating conditions such as the viscosity of the solution, the coating technique, and/or the appropriate solvent-removal phase. The coating, if present, may be applied to the prosthesis in its expanded configurations or even in its contracted state. Preferably, the coating is applied to the prosthesis in the contracted configuration.

The endolumenal prosthesis described herein has a structure that is useful for satisfying two roles, that is, flexibility and expansion/radial stiffness in two different states or configurations of the prosthesis. The high degree of flexibility in the non-expanded configuration and particularly in the clenched configuration permits easy insertion of the prosthesis even in ducts having particularly sinuous pathways. Moreover, in the expanded configuration, the prosthesis exhibits an unusual capacity to maintain the longitudinal shape of the lumen in which it is implanted. In particular, after the expansion of the prosthesis, distortion and deformation of the lumen from its natural orientation is prevented. Together with these advantages, this prosthesis is of unusually simple construction and in particular is easy to clench or crimp onto an SDS. The prosthesis of the invention is therefore particularly suitable for situations of implantation in ducts of complex geometry such as are often encountered in the field.

The prosthesis of the invention also has desirably uniform expansion even in the most extreme conditions, showing little or no distortion.

After expansion, the prosthesis has a configuration similar to that of a truss beam, which results in a high degree of radial stiffness. Moreover, when expanded, the prosthesis described herein has a strut-distribution density which is excellent for lining or supporting the duct and at the same time permitting and facilitating access to branches of the duct that are present in the section of the duct lined by the prosthesis. In particular, the prosthesis described herein is particularly suitable for use at bifurcations, for example, by means of branched catheters or catheters provided with lateral openings of the expansion devices.

It is particularly important to stress that the prosthesis described herein permits optimal support and lining of the ostial region of the lateral branch of a bifurcation (scaffolding).

By virtue of the prosthesis described herein, it is possible to achieve a uniform ratio between the prosthesis material and the vessel wall throughout the longitudinal extent of the prosthesis.

Moreover, it is possible to have uniform scaffolding throughout the portion of the vessel which is lined by the prosthesis and, by virtue of some embodiments having some circumferential lines that are not closed circumferentially, it is possible to have large openings precisely in the region of the lumen that is open to side branches.

By virtue to the stent described herein, over-stretching of the lumen is prevented and, with the use of SDS devices suitable for bifurcations, the prosthesis is positioned in a single procedure, avoiding the subsequent use of side-by-side or "kissing" balloons for shaping the portion of the prosthesis facing the mouth of the side branch of the bifurcation.

By virtue of the prosthesis described herein, it is possible constantly to maintain access to the side branch.

Other advantages of the prosthesis of the invention will be readily apparent to a person skilled in the art.

Naturally further variants and/or additions may be applied to the embodiments described and illustrated.

In order to satisfy contingent and specific requirements, a person skilled in the art may apply to the above-described preferred embodiment of the prosthesis many modifications, adaptations and replacements of elements with other functionally equivalent elements without, however, departing from the scope of the appended claims.

What is claimed is:

1. An expandable endoluminal prosthesis comprising, in its unexpanded configuration, a tubular body extending along a longitudinal axis and having a distal end and a proximal end;

the tubular body having a porous wall defined by a plurality of interlaced circumferential lines forming a pathway motif or pattern wherein at least one line is closed onto itself;

each of the lines extends along an axis; each of the lines comprises at least one plurality of modules;

each module comprises three lobes, that is, two outer lobes and one inner lobe disposed between the two outer lobes in the pathway of the pattern, said two outer lobes comprising:

a closer outer lobe having a first distance from the axis of the line of the module;

a farther outer lobe having a second distance from the axis of the line of the module, the second distance being greater than the first distance;

a first module of said plurality of modules comprises three lobes, a first and a second outer lobes of said module and a third inner lobe of said module;

a second module, adjoining said first module along said pathway, comprises three lobes, a fourth and fifth outer lobes of said second module and a sixth inner lobe of said second module;

each lobe of said plurality of modules comprising one or more curved sections having concavities facing in the same direction, a point far from said line axis of the module defining an apex of the lobe;

the lobes opening alternately on opposite sides of the pathway of the pattern along the extent of the line;

both of the outer lobes of the three lobes being extended by straight outer arms;

the at least one plurality of modules being arranged consecutively so as to have successive outer arms which extend from the outer lobes in substantially opposite directions relative to the pathway of the pattern for two successive modules; and wherein, for said first and adjoining second module, the distance between the apex of the first outer lobe and the apex of the third inner lobe of the same module is less than the distance between the apex of the same first lobe and the apex of the fourth or the fifth outer lobe of said adjoining module;

for each line, there is at least one adjacent line which has a motif that is a mirror image of said line with respect to an axis parallel to the axis of said line and said adjacent line;

at least one connecting element or bridge is provided between two adjacent lines, so that the facing outer lobes are directly opposite one another; and wherein said bridge extends and directly connects apexes of two facing closer outer lobes of said adjacent lines along a longitudinal axis parallel to the longitudinal axis of the tubular body.

2. A prosthesis according to claim 1, in which at least one of the outer arms extends along an axis which is inclined to the longitudinal axis of the tubular body and is also inclined to the axis of the line to which the module belongs.

3. A prosthesis according to claim 1 in which at least one outer arm of a module is shared with the adjacent module.

4. A prosthesis according to claim 1 in which the inner lobe is joined to the outer lobes by means of at least one inner arm.

5. A prosthesis according to claim 4 in which the inner lobe and the inner arm have an overall extent less than the overall extent of the outer lobes and the respective outer arms.

6. A prosthesis according to claim 1 in which the outer or inner arms have an extent which varies in the modules of the same line.

7. A prosthesis according to claim 1 in which the outer or inner arms have an extent which varies in the modules disposed along the longitudinal axis of the tubular body of the prosthesis.

8. A prosthesis according to claim 1 in which at least one module comprises at least one lobe comprising a plurality of curved sections with concavities having the same orientation and at least one interposed straight section.

9. A prosthesis according to claim 1 in which, in at least one line, two pluralities of modules are provided, alternating with one another so as to provide a series of a module of a first plurality and a module of the second plurality.

10. A prosthesis according to claim 1 in which, in at least one line, the same module is repeated along the pathway of the line in a mirror-image arrangement with respect to an axis parallel to the axis of the line.

11. A prosthesis according to claim 1 in which, in at least one line, the pathway is interrupted so as to form an opening in the pattern suitable for the passage of a stent delivery system guide wire.

12. A prosthesis according to claim 11 in which the pathway is interrupted to an extent equal to five lobes.

13. A prosthesis according to claim 11 in which the pathway is interrupted between two connecting bridges between the line and adjoining lines.

14. A prosthesis according to claim 1 in which at least one module is substantially M-shaped and is arranged so as to have outer arms directed substantially either towards the distal end or towards the proximal end of the prosthesis.

15. A prosthesis according to claim 1 in which the axis of the line is substantially perpendicular to the longitudinal axis of the tubular body.

16. A prosthesis according to claim 1 in which the axis of the line is inclined to the longitudinal axis at an angle of between 5 degrees and 45 degrees and preferably between 10 and 30 degrees.

17. A prosthesis according to claim 1 in which the line axis is straight or circumferential.

18. A prosthesis according to claim 1 in which the bridge comprises at least one bridge lobe.

19. A prosthesis according to claim 1 in which, along the line, a bridge is provided between two adjacent lines, for every first or second outer lobe having the same orientation.

20. A prosthesis according to claim 1 in which, between two adjacent lines, a continuous closed pathway is provided, disposed between two bridges defining a cell.

21. A prosthesis according to claim 20 in which a variation of the cell perimeter is provided along the longitudinal axis of the prosthesis.

22. A prosthesis according to claim 1 in which the prosthesis comprises an external or internal coating.

23. A prosthesis according to claim 22 in which the coating comprises a drug.

* * * * *